United States Patent
Harmon et al.

(10) Patent No.: US 6,545,140 B1
(45) Date of Patent: Apr. 8, 2003

(54) DNA ENCODING AN AVIAN BETA-DEFENSIN AND USES THEREOF

(75) Inventors: Barry G. Harmon, Athens, GA (US); Mark W. Jackwood, Watkinsville, GA (US); Charles W. Brockus, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/351,657

(22) Filed: Jul. 13, 1999

Related U.S. Application Data
(60) Provisional application No. 60/092,668, filed on Jul. 13, 1998.

(51) Int. Cl.⁷ ............................................. C07H 21/04
(52) U.S. Cl. ................... 536/23.5; 536/23.1; 536/23.4; 514/44; 435/69.9; 435/69.1
(58) Field of Search ................... 530/866, 317, 530/324, 300; 424/405; 435/375, 172.3, 69.9, 69.1; 514/12, 13, 14, 44; 536/23.5, 23.4, 23.1

(56) References Cited

U.S. PATENT DOCUMENTS

| | | | |
|---|---|---|---|
| 5,202,420 A | 4/1993 | Zasloff et al. | 530/324 |
| 5,459,235 A | 10/1995 | Selsted et al. | 530/300 |
| 5,519,115 A * | 5/1996 | Mapelli et al. | 530/324 |
| 5,631,144 A * | 5/1997 | Lemoine et al. | 435/69.9 |
| 5,635,594 A | 6/1997 | Lehrer et al. | 530/317 |
| 5,641,497 A * | 6/1997 | Bevin et al. | 424/405 |
| 5,656,738 A * | 8/1997 | Schonwetter et al. | 536/23.5 |
| 5,804,558 A * | 9/1998 | Lehrer et al. | 514/13 |
| 5,821,224 A * | 10/1998 | Selsted et al. | 514/12 |
| 5,837,510 A * | 11/1998 | Goldsmith et al. | 435/172.3 |
| 5,958,771 A * | 9/1999 | Bennett | 435/375 |
| 6,008,195 A * | 12/1999 | Selsted | 514/14 |
| 6,072,041 A * | 6/2000 | Davis et al. | 530/866 |

FOREIGN PATENT DOCUMENTS

WO 95/01095 * 1/1995

OTHER PUBLICATIONS

Lehninger, Principles of Biochemistry, p. 897, Chapter 29, Figure 29–22, 1982.*
Bensch, KW et al, FEBS Letters, vol. 368(2), pp. 331–335, Jul. 17, 1995.*
Evans, E.W., et al., "Antimicrobial Activity of Chicken and Turkey Heterophil Pepetides CHP1, CHP2, THP1, and THP3", *Veterinary Microbiology*, 47, 295–303, (1995).
Evans, E.W., et al., "Isolation of Antimicrobial Peptides from Avian Heterophils", *Journal of Leukocyte Biology*, 56(5), 661–665, (1994).

(List continued on next page.)

Primary Examiner—Lynette R. F. Smith
Assistant Examiner—Ginny Allen Portner
(74) Attorney, Agent, or Firm—Schwegman, Lundberg, Woessner & Kluth, P.A.

(57) ABSTRACT

An isolated nucleic acid molecule encoding avian beta-defensin is provided. Further provided are compositions comprising an avian beta-defensin, or portions thereof.

15 Claims, 11 Drawing Sheets

OTHER PUBLICATIONS

Evans, W.E., "Isolation of Antimicrobial Cationic Peptides From Chicken Heterophils", *Doctor of Philosophy Thesis, University of Georgia,* 1–150, (1994).

Harwig, S.S., et al., "Gallinacins: Cysteine–rich Antamicrobial Peptides of Chicken Leukocytes", *FEBS Letters, 342,* 281–285, (1994).

Martin, E., et al., "Defensins and Other Endonenous Peptide Antibiotics of Vertebrates.", *Jornal of Leukocyte Biology, 58*(2), 128–136, (Aug. 1995).

Michaelson, D., et al., "Cationic Defensins Arise From Charge–neutralized Propeptides: A Mechanism for Avoiding Leukocyte Autocytotoxicity?", *Journal of Leukocyte Biology, 51*(6), 634–639, (Jun., 1992).

Selsted, M.E., et al., "Purification, Primary Structure, and Antimicrobial Activities of a Guinea Pig Neutrophil Defensin.", *Infection and Immunity, 55*(8), 2281–2286, (Aug. 1987).

Selsted, M.E., et al., "Purification, Primary Structures, and Antibacterial Activities of β–Defensins, a New Family of Antimicrobial Peptides From Bovine Neutophils", *The Journal of Biologicl Chemistry, 268*(9), 6641–6648, (Mar., 1993).

Valore, E.V., et al., "Intramolecular Inhibition of Human Defensin HNP–1 By Its Propiece", *The Journal of Clinical Investigation. 97*(7), 1624–1629, (Apr., 1996).

* cited by examiner

Gal 2 mRNA   M R I L Y L L F S L F F
tatccgcagctcagcagatctgcagccATGAGGATTCTTTACCTGCTTTTCTCTCTCCTCTTCC
L A L Q V S P G L S S P R R D M   L F
TGGCACTCCAGGTTTCTCCAGGGTTGTCTTCGCCCCGGCGGGACATGCTGTTC
  C   K   G   G   S   C   H   F   G   G   C   P   S   H   L   I   K   V
TGTAAAGGAGGGTCCTGCCACTTTGGAGGGTGTCCCAGCCATCTAATCAAAGT
    G   S   C   F   G   F   R   S   C   C   K   W   P   W   N   A
CGGAAGCTGCTTCGGGTTCCGTTCCTGCTGCAAATGGCCTTGGAATGCA taaac
acttcatgagtccatcaagagctttgaaaatttcttccaggcatgtgctttaaatgctacagcaaaagcctcagcagcaagaagacccctctcatgtgttaatgca
atatgttttgtgttgtagagtaaatacaaatatcttctgcactgcctttcttcctcttgaataaattgtcattgcatagcaaaaaaa         (409)

Gal 1 mRNA
ggatgcacgctgttcttggtggggttcttacttccttgctgtaccctgagaaaccattgtcagccctgtgaaaacccgggacagac
       M R I V Y L L L P F I L L L A Q
gtaaaccATGCGGATCGTGTACCTGCTCCTCCCCTTCATCCTCCTCCTGGCCCAGG
G A A G S S Q A L   G   R   K   S   D   C   F   R   K
GTGCTGCAGGATCCTCCCAGGCTCTAGGAAGGAAGTCAGATTGTTTTCGAAA
    S   G   F   C   A   F   L   K   C   P   S   L   T   L   I   S   G
GAGTGGCTTCTGTGCATTTCTGAAGTGCCCTTCCCTCACTCTCATCAGTGGGA
  K   C   S   R   F   Y   L   C   C   K   R   I   W   G
AATGCTCAAGATTTTACCTCTGCTGCAAAAGAATATGGGGC tgaagagccagaca
tcccaagcaggacatcaccctggcttctcgcttctggaaacttccccattgacctctccccttcccacctctgcagtctcccatggtgtgagcgtggcagtag
aagttggagacatcccaccatgggcctgcagttgtttggccagttgctgcttttccctgctgaataaaggtgtgcagtttagcattgcaaaaa        (494)

THP 1 mRNA
ggatgcacgctgttgttggtggggttcctactgccttgctgtactctgagaaaccatcttcagctctgtgaaaagctgggacagg
       M R I V Y L L F P F I L L L A Q
cgtaaaccATGCGGATCGTGTACCTGCTCTTCCCCTTCATCCTCCTCCTGGCCCAG
G A A G S S L A L   G   K   R   E   K   C   L   R   R
GGTGCTGCAGGGTCCTCCCTGGCTTTAGGAAAAAGGGAAAAATGTTTACGTCG
    N   G   F   C   A   F   L   K   C   P   T   L   S   V   I   S   G
GAATGGCTTCTGCGCATTTCTGAAGTGCCCTACCCTCTCAGTCATCAGTGGGA
  T   C   S   R   F   Q   V   C   C   K   T   L   L   G
CATGTTCAAGATTTCAAGTCTGCTGCAAAACGTTATTGGGC tgaagagccggacttccc
aagcaggacatcgcttctgcttctcacttctggcaacatcccccactgacctctcccccttcccacctctgcagtctcccatggtgtgaccgtggcagtggaagc
tgaagacatcccagcgtgggcctgcagttatttgcccagatgctgcttttcctgctgaataaaggcgtgcagtttggcattgcaaaaaa       (494)

THP 2 mRNA   M R I L Y L L F S L L F L
tatttgcagcttagcagatctgcagccATGAGGATTCTTTACCTGCTTTTCTCTCTCCTCTTCCT
A L Q V S P G L S S P N R D M   L F
GGCACTCCAGGTTTCTCCAGGGTTGTCTTCACCCAACAGGGACATGTTGTTCT
  C   K   R   G   T   C   H   F   G   R   C   P   S   H   L   I   K   V
GTAAAGAGGGACCTGCCACTTTGGAAGGTGTCCCAGCCATCTAATCAAAGTT
    G   S   C   F   G   F   R   S   C   C   K   W   P   W   D   A
GGAAGCTGCTTTGGGTTCCGTTCCTGCTGCAAATGGCCATGGGATGCA taaaa
acttcatgagtctattcaagagctttggaaatttcttccaggaacttgctttaaatcccttcatgctacagcaaaacctcagcatcaagaaaactccttgcatgttt
aatgcaatatgttttgtgttatagagtaaatacaaatatcttctgtattgccttccttcctcttgaataaattgtcaatgttgcatagcatcaaaaaa     (424)

FIG. 1

Gal2

```
tatcgcagc tcagcagatc tgcagcc ATG AGG ATT CTT TAC CTG CTT TTC TCT      54
                              Met Arg Ile Leu Tyr Leu Leu Phe Ser
                               1               5

CTC CTC TTC CTG GCA CTC CAG GTT TCT CCA GGG TTG TCT TCG CCC CGG      102
Leu Leu Phe Leu Ala Leu Gln Val Ser Pro Gly Leu Ser Ser Pro Arg
 10              15                  20                  25

CGG GAC ATG ███ ███ ███ ███ ███ ███ ███ ███ ███ ███ ███ ███ ███      150
Arg Asp Met ███ ███ Cys ███ ███ ███ ███ Cys ███ ███ ███ ███ Cys
                30              35                  40

███ ███ ███ ███ ███ ███ ███ ███ ███ ███ ███ ███ ███ ███ ███ ███      198
███ ███ ███ ███ ███ ███ ███ ███ Cys ███ ███ ███ ███ Cys
         45                  50                  55

███ ███ ███ ███ ███ ███ taaacactto atgagtccat caagagcttt             249
Cys ███ ███ ███ ███ ███
         60 gaaaatttct tccaggcatg tgctttaaat gctacagcaa agcctcagca gcaagaagac    309
ccctctcatg tgttaatgca atatgttttg tgttgtagag taaatacaaa tatcttctgc    369
actgccttc ttcctcttga ataaattgtc attgcatagc aaaaaaaaaa aaaa           423
```

TSP2

```
tatttgcagc ttagcagatc tgcagcc ATG AGG ATT CTT TAC CTG CTT TTC TCT     54
                              Met Arg Ile Leu Tyr Leu Leu Phe Ser
                               1               5

CTC CTC TTC CTG GCA CTC CAG GTT TCT CCA GGG TTG TCT TCA CCC AAG      102
Leu Leu Phe Leu Ala Leu Gln Val Ser Pro Gly Leu Ser Ser Pro Lys
 10              15                  20                  25

AGG GAC ATG ███ ███ ███ ███ ███ ███ ███ ███ ███ ███ ███ ███ ███      150
Arg Asp Met ███ ███ Cys ███ ███ ███ Cys ███ ███ ███ ███ Cys
                30              35                  40

███ ███ ███ ███ ███ ███ ███ ███ ███ ███ ███ ███ ███ ███ ███ ███      198
███ ███ ███ ███ ███ ███ ███ ███ Cys ███ ███ ███ ███ Cys
         45                  50                  55

███ ███ ███ ███ ███ ███ taaaaacttc atgagtctat tcaagagctt             249
Cys ███ ███ ███ ███ ███ ███
         60 tggaaattc ttcaggaac ttgctttaaa tcccttcat gctacagcaa aacctcagca       309
tcagaaaac tccttgcatg ttaatgcaa tatgttttgt gttatagagt aaatacaaat      369
atcttctgta ttgccttcct tcctcttgaa taaattgtca atgttgcata gcatcaaaaa    429
aaaaaa                                                               435
```

FIG. 2A

TAP

```
cgccgagccg ctcgggacgg cagc ATG AGG CTC CAT CAC CTG CTC CTC GCG        51
                          Met Arg Leu His His Leu Leu Leu Ala
                           1               5

CTC CTC TTC CTG GTC CTG TCT GCT TGG TCA GGA TTT ACT CAA GGA GTA         99
Leu Leu Phe Leu Val Leu Ser Ala Trp Ser Gly Phe Thr Gln Gly Val
 10              15                  20                  25

GGA AAC CCG GTG AGC TGT GTG AGA AAG AAG GGC ATC TGC GTG CCC ATC        147
Gly Asn Pro Val Ser Cys Val Arg Lys Lys Gly Ile Cys Val Pro Ile
         30                  35                  40

AGG TGT CCT GGA AGC ATG AAA CAG ATT GGA ACA TGT GTG GGC AGA GCA        195
Arg Cys Pro Gly Ser Met Lys Gln Ile Gly Thr Cys Val Gly Arg Ala
     45                  50                  55

GTT AAA TGC TGT AGA AAG AAG taaagaagg ccaagacaca gccgggatca            246
Val Lys Cys Cys Arg Lys Lys
             60 atgcccagtc agaaactgcg ccctttgaca gagcgtctaa aatttaaacc agaatamatt     306
ttgttcaaag ttaaaaaaaa aaaaa                                            331
```

Gal1

```
ggatgcacgc tgttcttggt ggggttctta cttccttgct gtaccctgag aaaccattgt      60
cagcctgtg aaaaccgggg acagacgtaa acc ATG CGG ATC GTG TAC CTG CTC        114
                                    Met Arg Ile Val Tyr Leu Leu
                                     1               5

CTC CCC TTC ATC CTC CTG CTG GCC CAG GGT GCT GCA GGA TCC TCC CAG        162
Leu Pro Phe Ile Leu Leu Leu Ala Gln Gly Ala Ala Gly Ser Ser Gln
 10              15                  20

GCT CTA GGA ACG AAG TCA GTT TGT TTC AGA ACG AGC GTC TGT GCA            210
Ala Leu Gly Arg Lys Ser Val Cys Phe Arg Lys Ser Gly Lys Cys Ala
         25                  30                  35

TGT CGG AAC TGC CGT TGC CTG ACT GTG AGC AGT GAA TGC TCA AGA            258
Phe Leu Lys Cys Arg Asn Leu Thr Leu Ile Ser Glu Cys Ser Arg
 40              45                  50                  55

GTT TAC CTC TGC TGC AAG AGG ATA TGG GGT tgaagagcca gacatcccaa         309
Phe Tyr Leu Cys Cys Lys Arg Ile Trp Gly
             60              65 gcaggacatc acctggctt ctcgcttctg gaaacttccc ccattgacct ctcccttcc       369
cacctctgca gtctccatg gtgtgagcgt ggcagtagaa gttggagaca tccaccatg        429
ggcctgcagt tgtttggcca gttgctgctt ttccctgctg aataaaggtg tgcagtttag     488
cattgcaaaa aaaaaa                                                     504
```

FIG. 2B

TRP1

```
ggatgcaagc tgttgttggt gggttccta ctgcctgct gtactctgag aaaccatctt        60
cagctctgtg aaaagctggg acaggcgtaa acc ATG CGG ATC GTG TAC CTG CTC      114
                                    Met Arg Ile Val Tyr Leu Leu
                                     1                   5

TTC CCC TTC ATC CTC CTC CTG GCC CAG GGT GCT GCA GGG TCC TCC CTG       162
Phe Pro Phe Ile Leu Leu Leu Ala Gln Gly Ala Ala Gly Ser Ser Leu
         10                  15                      20

GCT TTA ... ... ... ... ... ... Cys ... ... ... ... ... ... Cys ...  210
Ala Leu ... ... ... ... ... ... Cys ... ... ... ... ... ... Cys Ala
     25                  30                      35

... ... ... ... ... ... ... ... ... ... ... ... ... ... ... ...      258
... ... Cys ... ... ... ... ... ... ... Cys ... ...
     40                  45                      50                   55

... ... ... ... ... ... ... ... tgaagagccg gacttcccaa                 303
Phe Gln Val Cys Cys ... ... ... ...
     60                  65 gcaggacatc gctttcgctt ctcacttctg gcaacatccc ccactgacct ctcccttcc      363
cacctgtgca gtctcccatg gtgtgaccgt ggcagtggaa gctgaagaca tccagcgtg      423
ggcctgcagt tatttgccca gatgctgctt tttcctgctg aataaaggcg tgcagtttgg     483
cattgcaaaa aaaaaaaa                                                   506
```

FIG. 2C

β-DEFENSINS

```
        SIGNAL/PROPIECE                              PEPTIDE
Gal 2
  + +                           +  +-       +    +     + +       +    +
MRILYLLFSLLFLALQVSPGLSSPRRDM    LF KGGS HFGG PSHLIKVGS FGFRS  KWPWNA

THP 2
  + +                              +-       ++   +   + +         +    +   -
MRILYLLFSLLFLALQVSPGLSSPNRDM    LF KRGT HFGR PSHLIKVGS FGFRS  KWPWDA

LAP
  + +  + +                        +          ++    +      +       +   +++
MRLHHLLLALLFLVLSAGSGFTQGVR    NSQS RRNKGI VPIR PGSMRQIGT LGAOVK  RRK

TAP
  + +  + +                        +          +     +      +      +  +  +++
MRLHHLLLALLFLVLSAWSGFTQGVG    NPVS VRNKGI VPIR PGSMKQIGT VGRAVK  RKK

THP 1
  ++                              ++- +  ++         +        +          +
MRIVYLLFPFILLLAQGAAGSSLAL    GKREK LRRNGF AFLK PTLSVISGT SRFQV  KTLLG

Gal 1
  ++                              +   -  ++         +        +         ++
MRIVYLLLPFILLLAQGAAGSSQAL    GRKSD FRKSGF AFLK PSLTLISGK SRFYL  KRIWG
```

CLASSICAL DEFENSINS

```
        SIGNAL                   PROPIECE
RatNP-3
  + +                +       -        + --    ---       -+     -       +
MRTLTLLTTLLLLALHTQA    ESPQGSTKEAPDEEQDISVFPGGDKGTALQDAAVKAGVT

PEPTIDE
     +      +     -+       +         +        +
 S RTSS RFGERLSGA RLNGRIYRL

SIGNAL                   PROPIECE
HNP-1
  + +                       -    +  --    -  -       --      +   ++
MRTLAILAAILLVALQAQA    EPLQARADEVAAAPEQIAADIPEVVVSLAWDESLAPKHPGSRKNM

PEPTIDE
     +       -++       +
A Y RIPA  AGERRYGT IYQGRLWAF
```

FIG. 3

| Amino Acid | Codon |
| --- | --- |
| Phe | UUU, UUC |
| Ser | UCU, UCC, UCA, UCG, AGU, AGC |
| Tyr | UAU, UAC |
| Cys | UGU, UGC |
| Leu | UUA, UUG, CUU, CUC, CUA, CUG |
| Trp | UGG |
| Pro | CCU, CCC, CCA, CCG |
| His | CAU, CAC |
| Arg | CGU, CGC, CGA, CGG, AGA, AGG |
| Gln | CAA, CAG |
| Ile | AUU, AUC, AUA |
| Thr | ACU, ACC, ACA, ACG |
| Asn | AAU, AAC |
| Lys | AAA, AAG |
| Met | AUG |
| Val | GUU, GUC, GUA, GUG |
| Ala | GCU, GCC, GCA, GCG |
| Asp | GAU, GAC |
| Gly | GGU, GGC, GGA, GGG |
| Glu | GAA, GAG |

FIG. 4

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

FIG. 5

|  | 5' | 11 | 21 | 31 | 41 | 51 |
|---|---|---|---|---|---|---|
|  | 1 GATATCATGG | AGATAATTAA | AATGATAACC | ATCTCGCAAA | GAAAGAAGGA | TGTGACTGTT |
| invhis2b.s | GATATCATGG | AGATAATTAA | AATGATAACC | ATCTCGCAAA | TAAATAAGTA | TTTTACTGTT |
| thp2p3fo.s | ---------- | ---------- | ---------- | ------TTNN | GNTTGTCGGC | NGTCNCTGTT |
|  | 5' | 71 | 81 | 91 | 1 | 11 |
|  | 61 TTCGTAACAG | TTTTGTAATA | AAAAACCTAT | AAATATGCCG | CGGGGTTCTC | ATCATCATCA |
| invhis2b.s | TTCGTAACAG | TTTTGTAATA | AAAAACCTAT | AAATATGCCG | CGGGGTTCTC | ATCATCATCA |
| thp2p3fo.s | TTCGTAACAG | TTTTGTAATA | AAAAACCTAT | AAATATGCCG | CGGGGTTCTC | ATCATCATCA |
|  | 5' | 31 | 41 | 51 | 61 | 71 |
|  | 121 TCATCATGGT | ATGGCTAGCA | TGACTGGTGG | ACAGCAAATG | GGTCGGGATC | TGTACGACGA |
| invhis2b.s | TCATCATGGT | ATGGCTAGCA | TGACTGGTGG | ACAGCAAATG | GGTCGGGATC | TGTACGACGA |
| thp2p3fo.s | TCATCATGGT | ATGGCTAGCA | TGACTGGTGG | ACAGCAAATG | GGTCGGGATC | TGTACGACGA |
|  | 5' | 91 | 1 | 11 | 21 | 31 |
|  | 181 TGACGATAAG | GATCCGAGCT | CGAGATCTGC | AGCCAGGACC | ATGAATACC | AACCTTGCAC |
| invhis2b.s | TGACGATAAG | GATCCGAGCT | CGAGATCTGC | AGCTGGTACC | ATGGAATTGG | AAGCTTGGAG |
| thp2p3fo.s | TGACGATAAG | GATCCGAGCT | CGAGATCTGC | AGCCATGAGG | ATTCTTTACC | TGCTTTTCTC |
|  | 5' | 51 | 61 | 71 | 81 | 91 |
|  | 241 TCGACTCTGC | CGAACACGAC | AAAATTCTCC | AGGAAGGTCC | CCACCCAAGA | AAAACAAAGG |
| invhis2b.s | TCGACTCTGC | TGAAGAGGAG | GAAATTCTCC | TTGAAGTTTC | CCTGGTGTTC | AAAGTAAAGG |
| thp2p3fo.s | TCTCCTCTTC | CTGGCACTCC | AGGTTTCTCC | AGGGTTGTCT | TCACCCAAGA | GGGACATGTT |
|  | 5' | 11 | 21 | 31 | 41 | 51 |
|  | 301 AGTCTGCAAA | AGACGCACCT | CCCACCACG | AACCGGCCCA | AGAAAACAAA | ACAAAGTGGG |
| invhis2b.s | AGTTTGCACC | AGACGCACCT | CTGTTCACTG | GTCCGGCGTA | TTAAAACACG | ATACATTGTT |
| thp2p3fo.s | GTTCTGTAAA | AGAGGGACCT | GCCACTTTGG | AAGGTGTCCC | AGCCATCTAA | TCAAAGTTGG |
|  | 5' | 71 | 81 | 91 | 1 | 11 |
|  | 361 AAGAGGACAT | GGATTAAGCG | CCAGATGCAA | AGCGCCATGG | AATGAAAAAA | AACTGCAGGA |
| invhis2b.s | ATTAGTACAT | TTATTAAGCG | CTAGATTCTG | TGCGTTGTTG | ATTTACAGAC | AATTGTTGTA |
| thp2p3fo.s | AAGCTGCTTT | GGGTTCCGTT | CCTGCTGCAA | ATGGCCATGG | GATGCATAAA | AACTTCATGA |

FIG. 8A

|  | 5' | 11 | 21 | 31 | 41 | 51 |
|---|---|---|---|---|---|---|
|  | 1 TTNNGNTTGT | CGGCNGTCNC | TGTTTTCGTA | ACAGTTTTGT | AATAAAAAAC | CTATAAATAT |
| ncbithp2.s | ---------- | ---------- | ---------- | ---------- | ---------- | ---------- |
| thp2p3fo.s | TTNNGNTTGT | CGGCNGTCNC | TGTTTTCGTA | ACAGTTTTGT | AATAAAAAAC | CTATAAATAT |
|  | 5' | 71 | 81 | 91 | 1 | 11 |
|  | 61 GCCGCGGGGT | TCTCATCATC | ATCATCATCA | TGGTATGGCT | AGCATGACTG | GTGGACAGCA |
| ncbithp2.s | ---------- | ---------- | ---------- | ---------- | ---------- | ---------- |
| thp2p3fo.s | GCCGCGGGGT | TCTCATCATC | ATCATCATCA | TGGTATGGCT | AGCATGACTG | GTGGACAGCA |
|  | 5' | 31 | 41 | 51 | 61 | 71 |
|  | 121 AATGGGTCGG | GATCTGTACG | ACGATGACGA | TAAAGATCCA | ACCTAGAGAT | CTGCAGCCAT |
| ncbithp2.s | ---------- | ---------- | ---------- | --TATTTGCA | GCTTAGAGAT | CTGCAGCCAT |
| thp2p3fo.s | AATGGGTCGG | GATCTGTACG | ACGATGACGA | TAAGGATCCG | AGCTCGAGAT | CTGCAGCCAT |
|  | 5' | 91 | 1 | 11 | 21 | 31 |
|  | 181 GAGGATTCTT | TACCTGCTTT | TCTCTCTCCT | CTTCCTGGCA | CTCCAGGTTT | CTCCAGGGTT |
| ncbithp2.s | GAGGATTCTT | TACCTGCTTT | TCTCTCTCCT | CTTCCTGGCA | CTCCAGGTTT | CTCCAGGGTT |
| thp2p3fo.s | GAGGATTCTT | TACCTGCTTT | TCTCTCTCCT | CTTCCTGGCA | CTCCAGGTTT | CTCCAGGGTT |
|  | 5' | 51 | 61 | 71 | 81 | 91 |
|  | 241 GTCTTCACCC | AAGAGGGACA | TGTTGTTCTG | TAAAAGAGGG | ACCTGCCACT | TTGGAAGGTG |
| ncbithp2.s | GTCTTCACCC | AAGAGGGACA | TGTTGTTCTG | TAAAAGAGGG | ACCTGCCACT | TTGGAAGGTG |
| thp2p3fo.s | GTCTTCACCC | AAGAGGGACA | TGTTGTTCTG | TAAAAGAGGG | ACCTGCCACT | TTGGAAGGTG |
|  | 5' | 11 | 21 | 31 | 41 | 51 |
|  | 301 TCCCAGCCAT | CTAATCAAAG | TTGGAAGCTG | CTTTGGGTTC | CGTTCCTGCT | GCAAATGGCC |
| ncbithp2.s | TCCCAGCCAT | CTAATCAAAG | TTGGAAGCTG | CTTTGGGTTC | CGTTCCTGCT | GCAAATGGCC |
| thp2p3fo.s | TCCCAGCCAT | CTAATCAAAG | TTGGAAGCTG | CTTTGGGTTC | CGTTCCTGCT | GCAAATGGCC |
|  | 5' | 71 | 81 | 91 | 1 | 11 |
|  | 361 ATGGGATGCA | TAAAAACTTC | ATGAGTCTAT | TCAAGAGCTT | TGGAAATCTC | TTCCAGGAAC |
| ncbithp2.s | ATGGGATGCA | TAAAAACTTC | ATGAGTCTAT | TCAAGAGCTT | TGGAAATTTC | TTCCAGGAAC |
| thp2p3fo.s | ATGGGATGCA | TAAAAACTTC | ATGAGTCTAT | TCAAGAGCTT | TGGAAATCTC | TTCCAGGANC |

FIG. 8B

SEQUENCE LISTING

<160> NUMBER OF SEQ ID NOS: 54

<210> SEQ ID NO 1
<211> LENGTH: 504
<212> TYPE: DNA
<213> ORGANISM: Gallus gallus

<400> SEQUENCE: 1

```
ggatgcacgc tgttcttggt ggggttctta cttccttgct gtaccctgag aaaccattgt      60
cagccctgtg aaaacccggg acagacgtaa accatgcgga tcgtgtacct gctcctcccc     120
ttcatcctcc tcctggccca gggtgctgca ggatcctccc aggctctagg aaggaagtca     180
gattgttttc gaaagagtgg cttctgtgca tttctgaagt gcccttccct cactctcatc     240
agtgggaaat gctcaagatt ttacctctgc tgcaaaagaa tatggggctg aagagccaga     300
catcccaagc aggacatcac cctggcttct cgcttctgga aacttccccc attgacctct     360
ccccttccca cctctgcagt ctcccatggt gtgagcgtgg cagtagaagt tggagacatc     420
ccaccatggg cctgcagttg tttggccagt tgctgctttt ccctgctgaa taaaggtgtg     480
cagtttagca ttgcaaaaaa aaaa                                            504
```

<210> SEQ ID NO 2
<211> LENGTH: 65
<212> TYPE: PRT
<213> ORGANISM: Gallus gallus

<400> SEQUENCE: 2

```
Met Arg Ile Val Tyr Leu Leu Leu Pro Phe Ile Leu Leu Leu Ala Gln
  1               5                  10                  15

Gly Ala Ala Gly Ser Ser Gln Ala Leu Gly Arg Lys Ser Asp Cys Phe
             20                  25                  30

Arg Lys Ser Gly Phe Cys Ala Phe Leu Lys Cys Pro Ser Leu Thr Leu
         35                  40                  45

Ile Ser Gly Lys Cys Ser Arg Phe Tyr Leu Cys Cys Lys Arg Ile Trp
     50                  55                  60

Gly
 65
```

<210> SEQ ID NO 3
<211> LENGTH: 423
<212> TYPE: DNA
<213> ORGANISM: Gallus gallus

<400> SEQUENCE: 3

```
tatccgcagc tcagcagatc tgcagccatg aggattcttt acctgctttt ctctctcctc      60
```

-continued

```
ttcctggcac tccaggttc tccagggttg tcttcgcccc ggcgggacat gctgttctgt      120
aaaggagggt cctgccactt tggagggtgt cccagccatc taatcaaagt cggaagctgc      180
ttcgggttcc gttcctgctg caaatggcct tggaatgcat aaacacttca tgagtccatc      240
aagagctttg aaaatttctt ccaggcatgt gctttaaatg ctacagcaaa gcctcagcag      300
caagaagacc cctctcatgt gttaatgcaa tatgttttgt gttgtagagt aaatacaaat      360
atcttctgca ctgcctttct tcctcttgaa taaattgtca ttgcatagca aaaaaaaaa      420 aaa                                                                    423
```

<210> SEQ ID NO 4
<211> LENGTH: 64
<212> TYPE: PRT
<213> ORGANISM: Gallus gallus
<400> SEQUENCE: 4

```
Met Arg Ile Leu Tyr Leu Leu Phe Ser Leu Leu Phe Leu Ala Leu Gln
 1               5                  10                  15

Val Ser Pro Gly Leu Ser Ser Pro Arg Arg Asp Met Leu Phe Cys Lys
            20                  25                  30

Gly Gly Ser Cys His Phe Gly Gly Cys Pro Ser His Leu Ile Lys Val
        35                  40                  45

Gly Ser Cys Phe Gly Phe Arg Ser Cys Cys Lys Trp Pro Trp Asn Ala
    50                  55                  60
```

<210> SEQ ID NO 5
<211> LENGTH: 506
<212> TYPE: DNA
<213> ORGANISM: Meleagris gallopavo
<400> SEQUENCE: 5

```
ggatgcacgc tgttgttggt ggggttccta ctgccttgct gtactctgag aaaccatctt       60
cagctctgtg aaaagctggg acaggcgtaa accatgcgga tcgtgtacct gctcttcccc      120
ttcatcctcc tcctggccca gggtgctgca gggtcctccc tggctttagg aaaaagggaa      180
aaatgtttac gtcggaatgg cttctgcgca tttctgaagt gccctaccct ctcagtcatc      240
agtgggacat gttcaagatt tcaagtctgc tgcaaaacgt tattgggctg aagagccgga      300
cttcccaagc aggacatcgc tttcgcttct cacttctggc aacatccccc actgacctct      360
ccccttccca cctctgcagt ctcccatggt gtgaccgtgg cagtggaagc tgaagacatc      420
ccagcgtggg cctgcagtta tttgcccaga tgctgctttt tcctgctgaa taaggcgtg      480 cagtttggca ttgcaaaaaa aaaaaa                                            506
```

<210> SEQ ID NO 6
<211> LENGTH: 65
<212> TYPE: PRT
<213> ORGANISM: Meleagris gallopavo
<400> SEQUENCE: 6

```
Met Arg Ile Val Tyr Leu Leu Phe Pro Phe Ile Leu Leu Leu Ala Gln
 1               5                  10                  15

Gly Ala Ala Gly Ser Ser Leu Ala Leu Gly Lys Arg Glu Lys Cys Leu
            20                  25                  30

Arg Arg Asn Gly Phe Cys Ala Phe Leu Lys Cys Pro Thr Leu Ser Val
        35                  40                  45

Ile Ser Gly Thr Cys Ser Arg Phe Gln Val Cys Cys Lys Thr Leu Leu
```

-continued

```
         50                  55                  60
Gly
 65

<210> SEQ ID NO 7
<211> LENGTH: 435
<212> TYPE: DNA
<213> ORGANISM: Meleagris gallopavo

<400> SEQUENCE: 7
tatttgcagc ttagcagatc tgcagccatg aggattcttt acctgctttt ctctctcctc      60
ttcctggcac tccaggtttc tccagggttg tcttcaccca agagggacat gttgttctgt     120
aaaagaggga cctgccactt tggaaggtgt cccagccatc taatcaaagt tggaagctgc     180 tttggggttcc gttcctgctg caaatggcca tgggatgcat aaaaacttca tgagtctatt     240
caagagcttt ggaaatttct tccaggaact tgctttaaat ccccttcatg ctacagcaaa     300
acctcagcat caagaaaact ccttgcatgt ttaatgcaat atgttttgtg ttatagagta     360
aatacaaata tcttctgtat tgccttcctt cctcttgaat aaattgtcaa tgttgcatag     420
catcaaaaaa aaaaa                                                      435

<210> SEQ ID NO 8
<211> LENGTH: 64
<212> TYPE: PRT
<213> ORGANISM: Meleagris gallopavo

<400> SEQUENCE: 8

Met Arg Ile Leu Tyr Leu Leu Phe Ser Leu Leu Phe Leu Ala Leu Gln
  1               5                  10                  15

Val Ser Pro Gly Leu Ser Ser Pro Lys Arg Asp Met Leu Phe Cys Lys
                 20                  25                  30

Arg Gly Thr Cys His Phe Gly Arg Cys Pro Ser His Leu Ile Lys Val
             35                  40                  45

Gly Ser Cys Phe Gly Phe Arg Ser Cys Cys Lys Trp Pro Trp Asp Ala
         50                  55                  60

<210> SEQ ID NO 9
<211> LENGTH: 120
<212> TYPE: DNA
<213> ORGANISM: Gallus gallus

<400> SEQUENCE: 9
ggaaggaagt cagattgttt tcgaaagagt ggcttctgtg catttctgaa gtgcccttcc      60
ctcactctca tcagtgggaa atgctcaaga ttttacctct gctgcaaaag aatatggggc     120

<210> SEQ ID NO 10
<211> LENGTH: 40
<212> TYPE: PRT
<213> ORGANISM: Gallus gallus

<400> SEQUENCE: 10

Gly Arg Lys Ser Asp Cys Phe Arg Lys Ser Gly Phe Cys Ala Phe Leu
  1               5                  10                  15

Lys Cys Pro Ser Leu Thr Leu Ile Ser Gly Lys Cys Ser Arg Phe Tyr
                 20                  25                  30

Leu Cys Cys Lys Arg Ile Trp Gly
             35                  40
```

```
<210> SEQ ID NO 11
<211> LENGTH: 108
<212> TYPE: DNA
<213> ORGANISM: Gallus gallus

<400> SEQUENCE: 11
ctgttctgta aaggagggtc ctgccacttt ggagggtgtc ccagccatct aatcaaagtc      60
ggaagctgct tcgggttccg ttcctgctgc aaatggcctt ggaatgca                  108

<210> SEQ ID NO 12
<211> LENGTH: 36
<212> TYPE: PRT
<213> ORGANISM: Gallus gallus

<400> SEQUENCE: 12

Leu Phe Cys Lys Gly Gly Ser Cys His Phe Gly Gly Cys Pro Ser His
1               5                   10                  15

Leu Ile Lys Val Gly Ser Cys Phe Gly Phe Arg Ser Cys Cys Lys Trp
            20                  25                  30

Pro Trp Asn Ala
        35

<210> SEQ ID NO 13
<211> LENGTH: 120
<212> TYPE: DNA
<213> ORGANISM: Meleagris gallopavo

<400> SEQUENCE: 13
ggaaaaaggg aaaaatgttt acgtcggaat ggcttctgcg catttctgaa gtgccctacc      60
ctctcagtca tcagtgggac atgttcaaga tttcaagtct gctgcaaaac gttattgggc    120

<210> SEQ ID NO 14
<211> LENGTH: 40
<212> TYPE: PRT
<213> ORGANISM: Meleagris gallopavo

<400> SEQUENCE: 14

Gly Lys Arg Glu Lys Cys Leu Arg Arg Asn Gly Phe Cys Ala Phe Leu
1               5                   10                  15

Lys Cys Pro Thr Leu Ser Val Ile Ser Gly Thr Cys Ser Arg Phe Gln
            20                  25                  30

Val Cys Cys Lys Thr Leu Leu Gly
        35                  40

<210> SEQ ID NO 15
<211> LENGTH: 108
<212> TYPE: DNA
<213> ORGANISM: Meleagris gallopavo

<400> SEQUENCE: 15
ttgttctgta aagagggac ctgccacttt ggaaggtgtc ccagccatct aatcaaagtt       60
ggaagctgct ttgggttccg ttcctgctgc aaatggccat gggatgca                  108

<210> SEQ ID NO 16
<211> LENGTH: 36
<212> TYPE: PRT
<213> ORGANISM: Meleagris gallopavo

<400> SEQUENCE: 16

Leu Phe Cys Lys Arg Gly Thr Cys His Phe Gly Arg Cys Pro Ser His
1               5                   10                  15
```

Leu Ile Lys Val Gly Ser Cys Phe Gly Phe Arg Ser Cys Cys Lys Trp
            20                  25                  30

Pro Trp Asp Ala
        35

<210> SEQ ID NO 17
<211> LENGTH: 23
<212> TYPE: DNA
<213> ORGANISM: Artificial Sequence
<220> FEATURE:
<223> OTHER INFORMATION: A primer

<400> SEQUENCE: 17
gcgaattctg caggatccaa act                                          23

<210> SEQ ID NO 18
<211> LENGTH: 22
<212> TYPE: DNA
<213> ORGANISM: Artificial Sequence
<220> FEATURE:
<223> OTHER INFORMATION: A primer

<400> SEQUENCE: 18
gcgaattctg caggatccaa ac                                           22

<210> SEQ ID NO 19
<211> LENGTH: 20
<212> TYPE: DNA
<213> ORGANISM: Artificial Sequence
<220> FEATURE:
<221> NAME/KEY: modified_base
<222> LOCATION: 12, 15
<223> OTHER INFORMATION: I
<223> OTHER INFORMATION: A primer

<400> SEQUENCE: 19
tgycayttyg gnggntgycc                                              20

<210> SEQ ID NO 20
<211> LENGTH: 20
<212> TYPE: DNA
<213> ORGANISM: Artificial Sequence
<220> FEATURE:
<221> NAME/KEY: modified_base
<222> LOCATION: 9
<223> OTHER INFORMATION: I
<223> OTHER INFORMATION: A primer

<400> SEQUENCE: 20
gcrttccang gccayttrca                                              20

<210> SEQ ID NO 21
<211> LENGTH: 26
<212> TYPE: DNA
<213> ORGANISM: Artificial Sequence
<220> FEATURE:
<221> NAME/KEY: modified_base
<222> LOCATION: 3, 12, 18
<223> OTHER INFORMATION: I
<223> OTHER INFORMATION: A primer

<400> SEQUENCE: 21
ggnttytgyg cnttyytnaa rtgycc                                       26

<210> SEQ ID NO 22
<211> LENGTH: 18

```
<212> TYPE: DNA
<213> ORGANISM: Artificial Sequence
<220> FEATURE:
<221> NAME/KEY: modified_base
<222> LOCATION: 7
<223> OTHER INFORMATION: I
<223> OTHER INFORMATION: A primer

<400> SEQUENCE: 22
ccadatncky ttrcarca                                                 18

<210> SEQ ID NO 23
<211> LENGTH: 24
<212> TYPE: DNA
<213> ORGANISM: Gallus gallus

<400> SEQUENCE: 23
gcactccagg tttctccagg gttg                                          24

<210> SEQ ID NO 24
<211> LENGTH: 21
<212> TYPE: DNA
<213> ORGANISM: Gallus gallus

<400> SEQUENCE: 24
atgcggatcg tgtacctgct c                                             21

<210> SEQ ID NO 25
<211> LENGTH:
<212> TYPE:
<213> ORGANISM:

<400> SEQUENCE: 25

000

<210> SEQ ID NO 26
<211> LENGTH:
<212> TYPE:
<213> ORGANISM:

<400> SEQUENCE: 26

000

<210> SEQ ID NO 27
<211> LENGTH:
<212> TYPE:
<213> ORGANISM:

<400> SEQUENCE: 27

000

<210> SEQ ID NO 28
<211> LENGTH: 331
<212> TYPE: DNA
<213> ORGANISM: Bos taurus

<400> SEQUENCE: 28
cgccgagccg ctcgggacgc cagcatgagg ctccatcacc tgctcctcgc gctcctcttc    60
ctggtcctgt ctgcttggtc aggatttact caaggagtag gaaatcctgt aagctgtgtt   120
aggaataaag gcatctgtgt gccgatcagg tgtcctggaa gcatgaaaca gattggcacc   180
tgtgttgggc gggcagtaaa atgctgtaga aagaagtaaa agaaggccaa gacacagccg   240
ggatcaatgc ccagtcagaa actgcgccct ttgacagagc gtctaaaatt taaaccagaa   300
```

```
taaattttgt tcaaagttaa aaaaaaaaa a                              331
```

<210> SEQ ID NO 29
<211> LENGTH: 420
<212> TYPE: DNA
<213> ORGANISM: Artificial Sequence
<220> FEATURE:
<223> OTHER INFORMATION: A vector sequence

<400> SEQUENCE: 29

```
gatatcatgg agataattaa aatgataacc atctcgcaaa taaataagta ttttactgtt   60
ttcgtaacag ttttgtaata aaaaacctat aaatatgccg cggggttctc atcatcatca  120
tcatcatggt atggctagca tgactggtgg acagcaaatg ggtcgggatc tgtacgacga  180
tgacgataag gatccgagct cgagatctgc agctggtacc atggaattcg aagcttggag  240
tcgactctgc tgaagaggag gaaattctcc ttgaagtttc cctggtgttc aaagtaaagg  300
agtttgcacc agacgcacct ctgttcactg gtccggcgta ttaaaacacg atacattgtt  360
attagtacat ttattaagcg ctagattctg tgcgttgttg atttacagac aattgttgta  420
```

<210> SEQ ID NO 30
<211> LENGTH: 384
<212> TYPE: DNA
<213> ORGANISM: Artificial Sequence
<220> FEATURE:
<221> NAME/KEY: unsure
<222> LOCATION: 3, 4, 6, 15, 19
<223> OTHER INFORMATION: n is a or c or t or g
<223> OTHER INFORMATION: Sequence from THP recombinant virus

<400> SEQUENCE: 30

```
ttnngnttgt cggcngtcnc tgttttcgta acagttttgt aataaaaaac ctataaatat   60
gccgcggggt tctcatcatc atcatcatca tggtatggct agcatgactg gtggacagca  120
aatgggtcgg gatctgtacg acgatgacga taaggatccg agctcgagat ctgcagccat  180
gaggattctt tacctgcttt tctctctcct cttcctggca ctccaggttt ctccagggtt  240
gtcttcaccc aagagggaca tgttgttctg taaagaggg acctgccact ttggaaggtg  300
tcccagccat ctaatcaaag ttggaagctg ctttgggttc cgttcctgct gcaaatggcc  360
atgggatgca taaaaacttc atga                                        384
```

<210> SEQ ID NO 31
<211> LENGTH: 420
<212> TYPE: DNA
<213> ORGANISM: Artificial Sequence
<220> FEATURE:
<221> NAME/KEY: unsure
<222> LOCATION: 3, 4, 6, 15, 19, 419
<223> OTHER INFORMATION: n is a or c or t or g
<223> OTHER INFORMATION: Sequence from THP recombinant virus

<400> SEQUENCE: 31

```
ttnngnttgt cggcngtcnc tgttttcgta acagttttgt aataaaaaac ctataaatat   60
gccgcggggt tctcatcatc atcatcatca tggtatggct agcatgactg gtggacagca  120
aatgggtcgg gatctgtacg acgatgacga taaggatccg agctcgagat ctgcagccat  180
gaggattctt tacctgcttt tctctctcct cttcctggca ctccaggttt ctccagggtt  240
gtcttcaccc aagagggaca tgttgttctg taaagaggg acctgccact ttggaaggtg  300
tcccagccat ctaatcaaag ttggaagctg ctttgggttc cgttcctgct gcaaatggcc  360
```

```
atgggatgca taaaaacttc atgagtctat tcaagagctt tggaaatctc ttccagganc    420
```

<210> SEQ ID NO 32
<211> LENGTH: 420
<212> TYPE: DNA
<213> ORGANISM: Artificial Sequence
<220> FEATURE:
<223> OTHER INFORMATION: Vector sequence

<400> SEQUENCE: 32

```
gatatcatgg agataattaa aatgataacc atctcgcaaa gaaagaagga tgtcactgtt    60
ttcgtaacag ttttgtaata aaaaacctat aaatatgccg cggggttctc atcatcatca    120
tcatcatggt atggctagca tgactggtgg acagcaaatg ggtcgggatc tgtacgacga    180
tgacgataag gatccgagct cgagatctgc agccaggacc atgcaatacc aaccttgcac    240
tcgactctgc cgaacacgac aaaattctcc aggaaggtcc ccacccaaga aaacaaagg    300
agtctgcaaa agacgcacct cccaccacgg aaccggccca agaaaacaaa acaaagtggg    360
aagaggacat ggattaagcg ccagatgcaa agcgccatgg aatgaaaaaa aactgcagga    420
```

<210> SEQ ID NO 33
<211> LENGTH: 420
<212> TYPE: DNA
<213> ORGANISM: Artificial Sequence
<220> FEATURE:
<221> NAME/KEY: unsure
<222> LOCATION: 3, 4, 6, 15, 19
<223> OTHER INFORMATION: n is a or c or t or g
<223> OTHER INFORMATION: Vector sequence

<400> SEQUENCE: 33

```
ttnngnttgt cggcngtcnc tgttttcgta acagttttgt aataaaaaac ctataaatat    60
gccgcgggt tctcatcatc atcatcatca tggtatggct agcatgactg gtggacagca    120
aatgggtcgg gatctgtacg acgatgacga taaagatcca cctagagat ctgcagccat    180
gaggattctt tacctgcttt tctctctcct cttcctggca ctccaggttt ctccagggtt    240
gtcttcaccc aagagggaca tgttgttctg taaaagaggg acctgccact ttggaaggtg    300
tcccagccat ctaatcaaag ttggaagctg ctttgggttc cgttcctgct gcaaatggcc    360
atgggatgca taaaaacttc atgagtctat tcaagagctt tggaaatctc ttccaggaac    420
```

<210> SEQ ID NO 34
<211> LENGTH: 28
<212> TYPE: PRT
<213> ORGANISM: Gallus gallus

<400> SEQUENCE: 34

```
Met Arg Ile Leu Tyr Leu Leu Phe Ser Leu Leu Phe Leu Ala Leu Gln
  1               5                  10                  15

Val Ser Pro Gly Leu Ser Ser Pro Arg Arg Asp Met
             20                  25
```

<210> SEQ ID NO 35
<211> LENGTH: 28
<212> TYPE: PRT
<213> ORGANISM: Meleagris gallopavo

<400> SEQUENCE: 35

```
Met Arg Ile Leu Tyr Leu Leu Phe Ser Leu Leu Phe Leu Ala Leu Gln
  1               5                  10                  15

Val Ser Pro Gly Leu Ser Ser Pro Lys Arg Asp Met
```

20              25

<210> SEQ ID NO 36
<211> LENGTH: 26
<212> TYPE: PRT
<213> ORGANISM: Bos taurus

<400> SEQUENCE: 36

Met Arg Leu His His Leu Leu Leu Ala Leu Leu Phe Leu Val Leu Ser
1               5                   10                  15

Ala Gly Ser Gly Phe Thr Gln Gly Val Arg
            20              25

<210> SEQ ID NO 37
<211> LENGTH: 26
<212> TYPE: PRT
<213> ORGANISM: Bos taurus

<400> SEQUENCE: 37

Met Arg Leu His His Leu Leu Leu Ala Leu Leu Phe Leu Val Leu Ser
1               5                   10                  15

Ala Trp Ser Gly Phe Thr Gln Gly Val Gly
            20              25

<210> SEQ ID NO 38
<211> LENGTH: 25
<212> TYPE: PRT
<213> ORGANISM: Meleagris gallopavo

<400> SEQUENCE: 38

Met Arg Ile Val Tyr Leu Leu Phe Pro Phe Ile Leu Leu Leu Ala Gln
1               5                   10                  15

Gly Ala Ala Gly Ser Ser Leu Ala Leu
            20              25

<210> SEQ ID NO 39
<211> LENGTH: 25
<212> TYPE: PRT
<213> ORGANISM: Gallus gallus

<400> SEQUENCE: 39

Met Arg Ile Val Tyr Leu Leu Leu Pro Phe Ile Leu Leu Leu Ala Gln
1               5                   10                  15

Gly Ala Ala Gly Ser Ser Gln Ala Leu
            20              25

<210> SEQ ID NO 40
<211> LENGTH: 38
<212> TYPE: PRT
<213> ORGANISM: Bos taurus

<400> SEQUENCE: 40

Asn Ser Gln Ser Cys Arg Arg Asn Lys Gly Ile Cys Val Pro Ile Arg
1               5                   10                  15

Cys Pro Gly Ser Met Arg Gln Ile Gly Thr Cys Leu Gly Ala Gln Val
            20                  25                  30

Lys Cys Cys Arg Arg Lys
        35

<210> SEQ ID NO 41
<211> LENGTH: 38
<212> TYPE: PRT

<213> ORGANISM: Bos taurus

<400> SEQUENCE: 41

Asn Pro Val Ser Cys Val Arg Asn Lys Gly Ile Cys Val Pro Ile Arg
1               5                   10                  15

Cys Pro Gly Ser Met Lys Gln Ile Gly Thr Cys Val Gly Arg Ala Val
            20                  25                  30

Lys Cys Cys Arg Lys Lys
            35

<210> SEQ ID NO 42
<211> LENGTH: 19
<212> TYPE: PRT
<213> ORGANISM: Rattus norvegicus

<400> SEQUENCE: 42

Met Arg Thr Leu Thr Leu Leu Thr Thr Leu Leu Leu Ala Leu His
1               5                   10                  15

Thr Gln Ala

<210> SEQ ID NO 43
<211> LENGTH: 39
<212> TYPE: PRT
<213> ORGANISM: Rattus norvegicus

<400> SEQUENCE: 43

Glu Ser Pro Gln Gly Ser Thr Lys Glu Ala Pro Asp Glu Glu Gln Asp
1               5                   10                  15

Ile Ser Val Phe Phe Gly Gly Asp Lys Gly Thr Ala Leu Gln Asp Ala
            20                  25                  30

Ala Val Lys Ala Gly Val Thr
            35

<210> SEQ ID NO 44
<211> LENGTH: 29
<212> TYPE: PRT
<213> ORGANISM: Rattus norvegicus

<400> SEQUENCE: 44

Cys Ser Cys Arg Thr Ser Ser Cys Arg Phe Gly Glu Arg Leu Ser Gly
1               5                   10                  15

Ala Cys Arg Leu Asn Gly Arg Ile Tyr Arg Leu Cys Cys
            20                  25

<210> SEQ ID NO 45
<211> LENGTH: 19
<212> TYPE: PRT
<213> ORGANISM: Homo sapiens

<400> SEQUENCE: 45

Met Arg Thr Leu Ala Ile Leu Ala Ala Ile Leu Leu Val Ala Leu Gln
1               5                   10                  15

Ala Gln Ala

<210> SEQ ID NO 46
<211> LENGTH: 45
<212> TYPE: PRT
<213> ORGANISM: Homo sapiens

<400> SEQUENCE: 46

Glu Pro Leu Gln Ala Arg Ala Asp Glu Val Ala Ala Ala Pro Glu Gln

```
            1               5              10              15
Ile Ala Ala Asp Ile Pro Glu Val Val Ser Leu Ala Trp Asp Glu
                20              25              30
Ser Leu Ala Pro Lys His Pro Gly Ser Arg Lys Asn Met
            35              40              45

<210> SEQ ID NO 47
<211> LENGTH: 30
<212> TYPE: PRT
<213> ORGANISM: Homo sapiens

<400> SEQUENCE: 47

Ala Cys Tyr Cys Arg Ile Pro Ala Cys Ile Ala Gly Glu Arg Tyr
1               5              10              15
Gly Thr Cys Ile Tyr Gln Gly Arg Leu Trp Ala Phe Cys Cys
                20              25              30

<210> SEQ ID NO 48
<211> LENGTH: 268
<212> TYPE: DNA
<213> ORGANISM: Meleagris gallopavo

<400> SEQUENCE: 48
tatttgcagc ttagagatct gcagccatga ggattcttta cctgcttttc tctctcctct      60
tcctggcact ccaggtttct ccagggttgt cttcacccaa gagggacatg ttgttctgta    120
aaagagggac ctgccacttt ggaaggtgtc ccagccatct aatcaaagtt ggaagctgct    180
ttgggttccg ttcctgctgc aaatggccat gggatgcata aaaacttcat gagtctattc    240
aagagctttg gaaatttctt ccaggaac                                       268

<210> SEQ ID NO 49
<211> LENGTH: 64
<212> TYPE: PRT
<213> ORGANISM: Artificial Sequence
<220> FEATURE:
<223> OTHER INFORMATION: A peptide of formula (I).
<221> NAME/KEY: SITE
<222> LOCATION: 3, 4, 6, 7, 10, 11, 13, 15, 17, 21
<223> OTHER INFORMATION: Xaa is Ile, Leu or Val.
<221> NAME/KEY: SITE
<222> LOCATION: 32, 37, 44, 47, 55, 59
<223> OTHER INFORMATION: Xaa is His, Asn, Gln, Lys or Arg.
<221> NAME/KEY: SITE
<222> LOCATION: 29, 45, 46, 48, 64
<223> OTHER INFORMATION: Xaa is Ile, Val, Met, Ala, Nle or Leu.

<400> SEQUENCE: 49

Met Arg Xaa Xaa Tyr Xaa Xaa Phe Ser Xaa Xaa Phe Xaa Ala Xaa Gln
1               5              10              15
Xaa Ser Pro Gly Xaa Ser Ser Pro Arg Arg Asp Met Xaa Phe Cys Xaa
                20              25              30
Gly Gly Ser Cys Xaa Phe Gly Gly Cys Pro Ser Xaa Xaa Xaa Xaa Xaa
            35              40              45
Gly Ser Cys Phe Gly Phe Xaa Ser Cys Cys Xaa Trp Pro Trp Asn Xaa
        50              55              60

<210> SEQ ID NO 50
<211> LENGTH: 65
<212> TYPE: PRT
<213> ORGANISM: Artificial Sequence
<220> FEATURE:
<223> OTHER INFORMATION: A compound of formula (II)
<221> NAME/KEY: SITE
```

```
<222> LOCATION: 3, 4, 6-8, 11-14, 25, 30
<223> OTHER INFORMATION: Xaa is Ile, Leu or Val.
<221> NAME/KEY: SITE
<222> LOCATION: 27, 28, 33, 34, 55, 61, 62
<223> OTHER INFORMATION: Xaa is His, Asn, Gln, Lys or Arg.
<221> NAME/KEY: SITE
<222> LOCATION: 41, 46, 48, 49, 58, 63
<223> OTHER INFORMATION: Xaa is Ile, Val, Met, Ala, Nle or Leu.

<400> SEQUENCE: 50

Met Arg Xaa Xaa Tyr Xaa Xaa Xaa Pro Phe Xaa Xaa Xaa Xaa Ala Gln
 1               5                  10                  15

Gly Ala Ala Gly Ser Ser Gln Ala Xaa Gly Xaa Xaa Ser Xaa Cys Phe
             20                  25                  30

Xaa Xaa Ser Gly Phe Cys Ala Phe Xaa Lys Cys Pro Ser Xaa Thr Xaa
         35                  40                  45

Xaa Ser Gly Lys Cys Ser Xaa Phe Tyr Xaa Cys Cys Xaa Xaa Xaa Trp
     50                  55                  60

Gly
65

<210> SEQ ID NO 51
<211> LENGTH: 65
<212> TYPE: PRT
<213> ORGANISM: Artificial Sequence
<220> FEATURE:
<223> OTHER INFORMATION: A compound of formula (III)
<221> NAME/KEY: SITE
<222> LOCATION: 3, 4, 6, 7, 11-14, 23, 25
<223> OTHER INFORMATION: Xaa is Ile, Leu or Val.
<221> NAME/KEY: SITE
<222> LOCATION: 27, 28, 30, 33-35, 42, 55, 57, 61
<223> OTHER INFORMATION: Xaa is His, Asn, Gln, Lys or Arg.
<221> NAME/KEY: SITE
<222> LOCATION: 32, 39, 41, 46, 48, 49, 58, 63, 64
<223> OTHER INFORMATION: Xaa is Ile, Val, Met, Ala, Nle or Leu.

<400> SEQUENCE: 51

Met Arg Xaa Xaa Tyr Xaa Xaa Phe Pro Phe Xaa Xaa Xaa Xaa Ala Gln
 1               5                  10                  15

Gly Ala Ala Gly Ser Ser Xaa Ala Xaa Gly Xaa Xaa Glu Xaa Cys Xaa
             20                  25                  30

Xaa Xaa Xaa Gly Phe Cys Xaa Phe Xaa Xaa Cys Pro Thr Xaa Ser Xaa
         35                  40                  45

Xaa Ser Gly Thr Cys Ser Xaa Phe Xaa Xaa Cys Cys Xaa Thr Xaa Xaa
     50                  55                  60

Gly
65

<210> SEQ ID NO 52
<211> LENGTH: 63
<212> TYPE: PRT
<213> ORGANISM: Artificial Sequence
<220> FEATURE:
<223> OTHER INFORMATION: A compound of formula (IV)
<221> NAME/KEY: SITE
<222> LOCATION: 3, 4, 6, 7, 10, 11, 13, 15, 17, 20
<223> OTHER INFORMATION: Xaa is Ile, Leu or Val.
<221> NAME/KEY: SITE
<222> LOCATION: 31, 32, 36, 39, 43, 54, 58
<223> OTHER INFORMATION: Xaa is His, Asn, Gln, Lys or Arg.
<221> NAME/KEY: SITE
<222> LOCATION: 28, 44, 45, 47, 63
<223> OTHER INFORMATION: Xaa is Ile, Val, Met, Ala, Nle or Leu.

<400> SEQUENCE: 52
```

-continued

```
Met Arg Xaa Xaa Tyr Xaa Xaa Phe Ser Xaa Xaa Phe Xaa Ala Xaa Gln
 1               5                  10                 15

Xaa Pro Gly Xaa Ser Ser Pro Asn Arg Asp Met Xaa Phe Cys Xaa Xaa
            20              25              30

Gly Thr Cys Xaa Phe Gly Xaa Cys Pro Ser Xaa Xaa Xaa Lys Xaa Gly
        35              40              45

Ser Cys Phe Gly Phe Xaa Ser Cys Cys Xaa Trp Pro Trp Asp Xaa
    50              55              60
```

<210> SEQ ID NO 53
<211> LENGTH: 11
<212> TYPE: RNA
<213> ORGANISM: Gallus gallus

<400> SEQUENCE: 53
augcagccau g                                                          11

<210> SEQ ID NO 54
<211> LENGTH: 11
<212> TYPE: RNA
<213> ORGANISM: Gallus gallus

<400> SEQUENCE: 54
augaaaccau g                                                          11

DNA ENCODING AN AVIAN BETA-DEFENSIN AND USES THEREOF

CROSS-REFERENCE TO RELATED APPLICATIONS

This application is a continuation-in-part application of U.S. provisional application Ser. No. 60/092,668, filed Jul. 13, 1998, the disclosure of which is incorporated by reference herein.

STATEMENT OF GOVERNMENT RIGHTS

This invention was made with a grant from the Government of the United States of America (grant Nos. 9203470 and 9501832 from the United States Department of Agriculture). The Government may have certain rights to the invention.

BACKGROUND OF THE INVENTION

One of the defense mechanisms against infection by both animals and plants is the production of peptides that have antimicrobial and antiviral activity. Various classes of these peptides have been isolated from tissues of plants and animals. These classes include the tachyplesins (Nakamura et al., 1988), the "protegrins" (Kokryakov et al., 1993) and the defensins, which include beta-defensins and classical defensins. The defensins are characterized by six invariant cysteines and three intramolecular cystine disulfide bonds (Lehrer et al., 1991; Lehrer et al., 1993). Classical defensins are short (29–35 amino acid residues) cationic peptides containing three pair of disulfide-linked cysteines. Although beta-defensins are nearly identical in their three-dimensional structure to classical defensins, beta-defensins are slightly larger (38–42 amino acid residues) and differ in the spacing of the conserved cysteine residues and connectivity of the cysteine linkages relative to classical defensins (Zimmerman et al., 1995).

Heterophils are the major granulated leukocyte of birds and are similar to the mammalian neutrophil. Avian heterophils lack myeloperoxidase and alkaline phosphatase activities but their ultrastructure, cytochemistry, and functions are otherwise similar to mammalian neutrophils (Pennial and Spitznagel, 1975; Montali, 1988). Both heterophils and neutrophils possess cationic antimicrobial peptides, which are important mediators of innate disease resistance in tissues exposed to microbial pathogens. Cationic antimicrobial peptides likely exert their antimicrobial activity by interacting with cell membranes or viral envelopes initially via electrostatic forces then by membrane insertion in which they form voltage gated ion channels resulting in increased permeability (Boman, 1991; Kagan et al., 1990).

Numerous mammalian neutrophil classical defensins have been isolated and sequenced (Selsted and Harwig, 1987; Belcourt et al., 1992; Wilde et al., 1989; U.S. Pat. No. 5,202,420). Three chicken heterophil beta-defensin mature peptide amino acid sequences (Gal 1/CHP 1, Gal 1α/CHP 2, and Gal 2) (Harwig et al., 1994; Evans et al., 1994; U.S. Pat. No. 5,202,420) and three partial turkey heterophil beta-defensins (THP 1, THP 2, and THP 3) have been reported (Evans et al., 1994). These avian beta-defensins are bacteriocidal in vitro for both avian and human bacterial pathogens (Evans et al., 1995). Thirteen mature bovine neutrophil beta-defensins amino acid sequences have also been reported (Selsted et al., 1993; U.S. Pat. No. 5,459,235).

Defensins are synthesized as 93–95 residue prepro defensins with a hydrophobic 19 amino acid signal sequence which is necessary for insertion into the endoplasmic reticulum prior to transport to granules. It has been proposed that neutrophil storage granule peptides (classical defensins) have a negatively charged propiece (of about 40–45 amino acids) to neutralize or balance the positive charge of the mature peptide (Michaelson et al., 1992). This propiece also is necessary for proper peptide folding and in targeting of the mature peptide into storage granules (Liu and Ganz, 1995). Thus far, all characterized classical defensins from mammalian granulocytes and from intestinal Paneth cells have a negatively charged propiece (Jones and Bevins, 1993; Yount et al., 1995).

In contrast, storage granule-free epithelial cell beta-defensin propeptides of the respiratory and oral cavity, i.e., bovine tracheal antimicrobial peptide (TAP) and lingual antimicrobial peptide (LAP), have an abridged propiece that has no neutralizing negative charge (Diamond et al., 1991; Schonwetter et al., 1995). These antimicrobial peptides are synthesized de novo upon stimulation and are not stored in granules (Russell et al., 1996; Schonwetter et al., 1995). The propieces for beta-defensins found in bovine neutrophils have not been characterized (Selsted et al., 1993).

Thus, what is needed is the identification and isolation of a variety of genes encoding avian peptides having specific antimicrobial activities.

SUMMARY OF THE INVENTION

The invention provides an isolated and purified nucleic acid molecule comprising a nucleic acid sequence which encodes an avian beta-defensin, a biologically active fragment or a biologically active variant thereof. As described hereinbelow, the complete cDNA for two chicken (Gal 1/CHP 1 and Gal 2) and two turkey (THP 1 and THP 2) beta-defensins were obtained. Surprisingly, the four deduced beta-defensin pro regions lack the long, negatively charged propiece reported for classical defensin pro regions, a region which is thought to stabilize and inactivate the positively charged mature peptide and target the propeptide to the storage granule.

Preferred isolated nucleic acid molecules of the invention include those having a nucleic acid sequence comprising a full-length avian beta-defensin gene, i.e., encoding the pre-pro form of the peptide (i.e., one having the signal sequence and the propiece), e.g., a nucleic acid sequence comprising SEQ ID NO:1, SEQ ID NO:3, SEQ ID NO:5, SEQ ID NO:7, or a variant thereof, or comprising a nucleic acid sequence encoding the mature form of an avian beta-defensin, such as a nucleic acid sequence comprising SEQ ID NO:9, SEQ ID NO:11, SEQ ID NO:13, SEQ ID NO:15, or a variant thereof. Also preferably, the nucleic acid molecules of the invention encode a peptide having an amino acid corresponding to the prepro form of an avian beta-defensin, e.g., SEQ ID NO:2, SEQ ID NO:4, SEQ ID NO:6, SEQ ID NO:8, or a variant thereof, or an amino acid sequence corresponding to the mature form of an avian beta-defensin, such as SEQ ID NO:10, SEQ ID NO:12, SEQ ID NO:14, SEQ ID NO:16, or a variant thereof. It is preferred that the nucleic acid molecules of the invention encode a peptide having antimicrobial (e.g., antibacterial, antiviral, antiprotozoal or antifungal) activity, more preferably peptides having a broad spectrum (for example, they are active against a variety of bacteria of different genera) of antimicrobial activity.

It is also envisioned that anti-sense nucleic acid molecules, e.g., a molecule which is the complement of an avian beta-defensin, a biologically active fragment, variant thereof, are within the scope of the invention. The nucleic acid molecules of the invention, fragments or variants thereof, either DNA or RNA, are useful to prepare probes, primers or expression cassettes which, in turn, are useful to detect, amplify and express other avian beta-defensin genes and related genes.

Therefore, the invention also provides an expression cassette comprising: a DNA sequence which is operably linked to a promoter functional in a host cell, which DNA sequence encodes an avian beta-defensin, a biologically active fragment or a biologically active variant thereof. The host cell may be prokaryotic or eukaryotic in origin. These cassettes may be employed to prepare recombinant peptides. For example, an expression cassette of the invention may be introduced and expressed in a host cell, e.g., an insect cell using a baculovirus vector, so as to yield recombinant avian beta-defensin peptide, a biologically active fragment, or variant thereof. Preferably, the recombinant peptide is recovered from the host cell. It is preferred that a peptide of the invention is active against at least one pathogen including, but not limited to, *Staphylococcus aureus, Escherichia coli, Pasteurella multocida, Bordetella avium, Mycoplasma gallispeticum, Candida albicans, Listeria monocytogenes, Salmonella typhimurium, Salmonella enteriditis*, or *Campylobacter jejuni*.

Hence, the invention further provides an isolated and purified avian beta-defensin peptide, a biologically active variant or fragment thereof. Preferred peptides include the prepro form of an avian beta-defensin. More preferably, the peptide is a compound of formula (I):

GCPSX$^2$X$^3$X$^3$X$^2$X$^3$GSCFGFX$^2$SCCX$^2$WPWNX$^3$, SEQ ID NO:49 wherein X$^3$ is I, V, M, A, norleucine or L, wherein X$^2$ is H, N, Q, K or R, and wherein X$^1$ is I, L or V;

a compound of formula (II):

MRX$^1$VYX$^1$X$^1$X$^1$PFX$^1$X$^1$X$^1$X$^1$AQGAAGSSQAX$^1$G X$^2$X$^2$SX$^1$CFX$^2$X$^2$SGFCAFX$^3$KCPSX$^3$TX$^3$X$^3$SGKC SX$^2$FYX$^3$CCX$^2$X$^2$X$^3$WG, SEQ ID NO:50 wherein X$^3$ is I, V, M, A, norleucine or L, wherein X$^2$ is H, N, Q, K or R, and wherein X$^1$ is I, L, or a compound of formula (III):

MRX$^1$X$^1$YX$^1$X$^1$FPFX$^1$X$^1$X$^1$X$^1$AQGAAGSSX$^1$AX$^1$G X$^2$X$^2$EX$^2$CX$^3$X$^2$X$^2$X$^2$GFCX$^3$FX$^3$X$^2$CPTX$^3$SX$^3$X$^3$S GTCSX$^2$FX$^2$X$^3$CCX$^2$T X$^3$X$^3$G, SEQ ID NO:51 wherein X$^3$ is I, V, M, A, norleucine or L, wherein X$^2$ is H, N, Q, K or R, and wherein X$^1$ is I, L or V; or a compound of formula (IV):

MRX$^1$X$^1$YX$^1$X$^1$FSX$^1$X$^1$FX$^1$AX$^1$Q X$^1$PGX$^1$SSPNRD MX$^3$FCX$^2$X$^2$GTCX$^2$FGX$^2$CPSX$^2$X$^3$X$^3$KX$^3$GSCFG FX$^2$SCCX$^2$WPWDX$^3$, S SEQ ID NO:52 wherein X$^3$ is I, V, M, A, norleucine or L, wherein X$^2$ is H, N, Q, K or R, and wherein X$^1$ is I, L or V.

The recombinant peptide may be recovered from cell lysates in a soluble fraction, in the insoluble fraction, or from supernatants, i.e., the recombinant peptide is secreted into the extracellular environment of the host cell. Another embodiment of the invention is a fusion polypeptide comprising at least a portion of the avian beta-defensin peptide and at least a portion of a second polypeptide. These peptides are useful as antibiotic, disinfectants, antimicrobials in biological products, food preservatives or to treat food products, such as crops, shell fish and poultry, to eliminate potential pathogens. The peptides may also promote wound healing and tissue repair. Preferably, the isolated peptides of the invention have substantially the same antimicrobial activity as a peptide having SEQ ID NO:2, SEQ ID NO:4, SEQ ID NO:6, SEQ ID NO:8, SEQ ID NO:10, SEQ ID NO:12, SEQ ID NO:14, SEQ ID NO:16, or a variant thereof. These isolated peptides, or nucleic acid molecules encoding them, may also be useful to study microbial resistance to heterophil microbicidal activity, and the relationship between disease resistance and a particular avian beta-defensin peptide. Further, quantitation of avian beta-defensin by immunoassay, using recombinant peptide as a standard, or other such methods well known in the art, or measurement of avian beta-defensin RNA by well known hybridization techniques may serve as a diagnostic tool for infections.

Further provided is a composition comprising an amount of an isolated and purified avian beta-defensin, a variant, a derivative, or a combination thereof, in combination with a pharmaceutically acceptable carrier, such as an injectable or ingestible liquid carrier. Such a composition is useful in a method to treat or prevent a vertebrate having or at risk of having a microbial infection. Thus, the method comprises contacting a vertebrate, e.g., a bird or a human, with an amount of isolated and purified avian beta-defensin, a variant, a fragment, a derivative, or a combination thereof, effective to prevent, reduce or inhibit the infection.

Also provided is a method to prepare or identify poultry having genetically mediated superior disease resistance. The method comprises contacting a probe having at least a portion of a nucleic acid molecule of the invention with a nucleic acid sample obtained from a bird so as to form binary complexes. Then, the amount or presence of the complexes is detected or determined. Preferably such a method is used to breed poultry having certain avian beta-defensin genes. Moreover, the nucleic acid molecules of the invention may also be useful as a marker for various genetic studies. This type of marker can be used to diagnose genetic diseases which may be linked to this marker, if not directly due to a defect in the avian beta-defensin gene, as well as in restriction fragment length polymorphism (RFLP) studies for breeding purposes.

The invention also includes a method to prepare a transgenic vertebrate, such as an avian, having superior disease resistance. For example, the method comprises introducing into an avian embryo or germ cell of a bird a nucleic acid molecule of the invention so as to obtain a transgenic avian. Further provided is a transgenic vertebrate, whose cells contain a recombinant DNA sequence, wherein the recombinant DNA sequence comprises a transcriptional control sequence and a DNA segment encoding an avian beta-defensin. Preferably, the transcriptional control sequence and the DNA segment encoding an avian beta-defensin are operatively linked to each other and are integrated into the genome of the vertebrate. The DNA segment is expressed in the transgenic vertebrate so as to result in the transgenic vertebrate having increased amounts of avian beta-defensin. Methods to prepare transgenic avians are disclosed, for example, in U.S. Pat. No. 5,162,215 and WO 97/47739.

Also provided is a method for detecting nucleic acid encoding an avian beta-defensin peptide. The method comprises contacting an amount of DNA or RNA obtained from a vertebrate physiological sample which comprises cells suspected of containing DNA or RNA encoding the peptide with an amount of at least two oligonucleotides under conditions effective to amplify the DNA, or reverse transcribe the RNA and then amplify the DNA, by, e.g., a polymerase chain reaction, so as to yield an amount of amplified DNA. At least one oligonucleotide is specific for DNA encoding the avian beta-defensin. The presence of the amplified DNA is then detected or determined. Preferably, the amplified DNA is subjected to agarose gel electrophoresis prior to detection.

Thus, the invention also provides a diagnostic kit for detecting the presence of nucleic acid encoding avian beta-defensin in a sample. The kit comprises packaging containing (a) a known amount of a first oligonucleotide, wherein the first oligonucleotide consists of at least about 7 to about 50 nucleotides, preferably at least about 12 to about 15 nucleotides, and wherein the oligonucleotide has at least about 70% contiguous nucleotide sequence identity to SEQ ID NO:1, SEQ ID NO:3, SEQ ID NO:5, SEQ ID NO:7, SEQ ID NO:9, SEQ ID NO:11, SEQ ID NO:13, or SEQ ID NO:15; and (b) a known amount of a second oligonucleotide, wherein the second oligonucleotide consists of at least about 7 to about 50 nucleotides, preferably at least about 12 to about 15 nucleotides, and wherein the oligonucleotide has at least about 70% contiguous sequence identity to a nucleotide sequence which is complementary to SEQ ID NO:1, SEQ ID NO:3, SEQ ID NO:5, SEQ ID NO:7, SEQ ID NO:9, SEQ ID NO:11, SEQ ID NO:13 or SEQ ID NO:15.

BRIEF DESCRIPTION OF THE FIGURES

FIG. 1. Nucleic acid sequence encoding, and inferred amino acid sequence of, the prepro form of Gal 1 (SEQ ID NO:1 and SEQ ID NO:2, respectively; Genbank Accession No. AF033335), Gal 2 (SEQ ID NO:3 and SEQ ID NO:4, respectively; Genbank Accession No. AF033336), THP 1 (SEQ ID NO:5 and SEQ ID NO:6, respectively; Genbank Accession No. AF033337), and THP 2 (SEQ ID NO:7 and SEQ ID NO:8, respectively; Genbank Accession No. AF033338). The prepro-region is highlighted in light gray, and the polyadenylation signal underlined. Mature forms of Gal1 (SEQ ID NO:10 encoded by SEQ ID NO:9), Gal2 (SEQ ID NO:12 encoded by SEQ ID NO:11), THP1 (SEQ ID NO:14 encoded by SEQ ID NO:13) and THP2 (SEQ ID NO:16 encoded by SEQ ID NO:15) are also shown.

FIG. 2. Nucleic acid sequence comparison of Gal 1, Gal 2, THP 1, THP 2, and bovine tracheal antimicrobial peptide (bTAP). The prepro peptide coding sequences are shown in capital letters with cysteine residues highlighted in white. The mature peptide is highlighted in light gray. The polyadenylation site is single underlined, and the Kozak box is double underlined.

FIG. 3. Charge balance distribution and relationship of beta-defensins; Gal 2, Gal 1, THP 2, THP 1, TAP, and LAP, with classical defensins (Human Neutrophil Peptide-1, HNP-1; Rat Neutrophil Peptide-3, RatNP-3). The signal/pro region length is also compared. The six invariant cysteines are highlighted in the mature peptide sequences. The symbol for histidine charge is+due to its pH dependency.

FIG. 4. Codons for specified amino acids.

FIG. 5. Exemplary and preferred amino acid substitutions for variant peptides or polypeptides of the invention.

FIG. 8. (A) invhis2b=baculovirus vector sequence. thp2p3fo=sequence from THP recombinant virus. Nucleotides outlined in yellow represent nucleotides found in the THP recombinant virus that are consistent with the known sequence of the baculovirus transfer vector. Nucleotides outlined in green encode for the His-tag of the fusion peptide. Pink outlined nucleotides found in the THP recombinant virus that encode for THP 2. (B) ncbithp2=THP cDNA sequence. thp2p3fo=sequence from the THP recombinant virus. Nucleotides outlined in yellow are from baculovirus vector. Nucleotides outlined in green encode the His-tag of the fusion peptide. The nucleotides outlined in pink represent nucleotides found in the THP 2 recombinant virus that are consistent with the known sequence encoding THP2.

DETAILED DESCRIPTION OF THE INVENTION

Definitions

Figure 6:
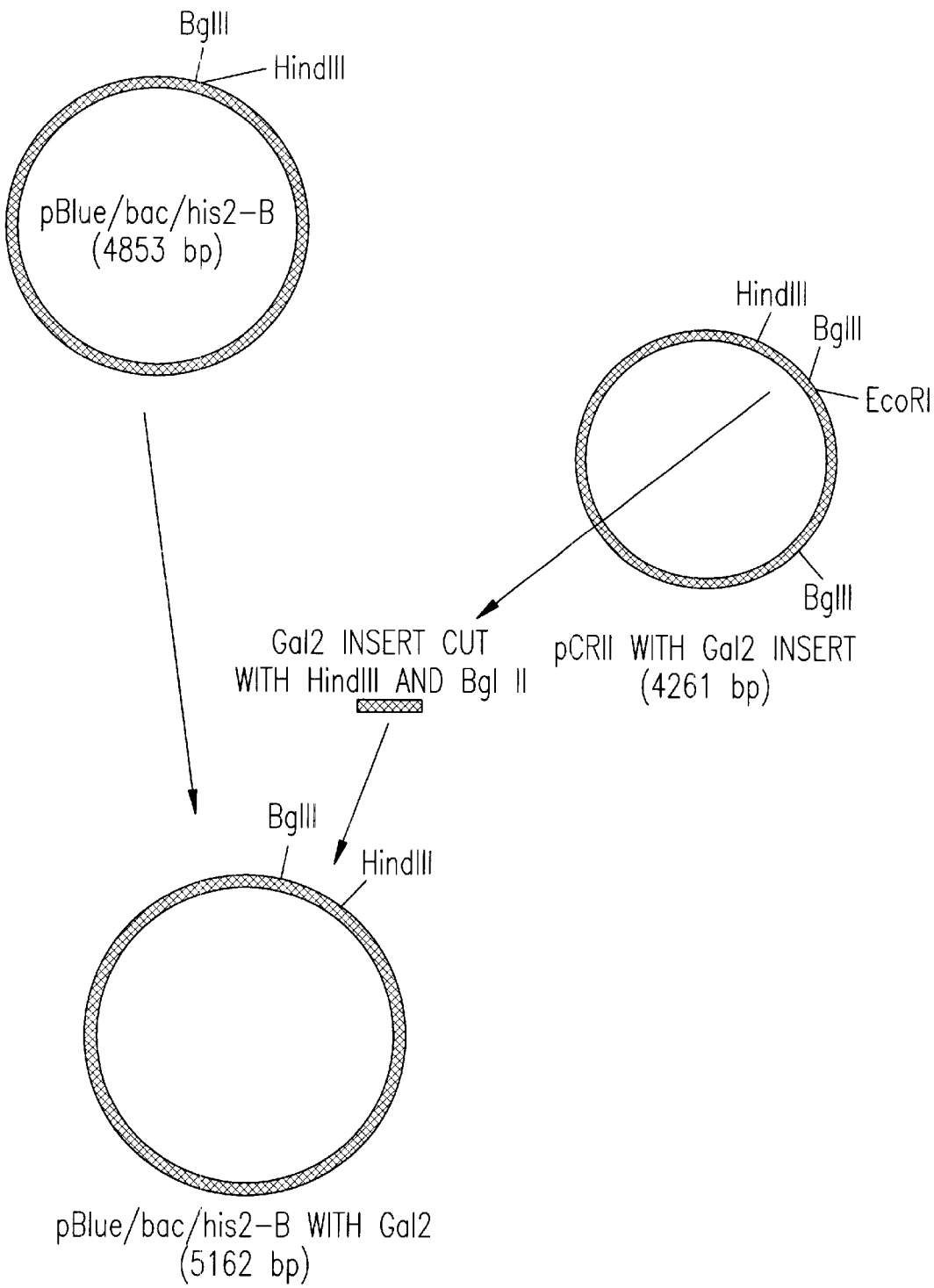
FIG. 6. Construction of recombinant transfer vector, pBlueBacHis2B, containing gallinacin 2 cDNA insert.

As used herein, a "peptide" of the invention refers to the prepro, pro or mature form of a peptide, which comprises no more than about 75, preferably about. 10 to about 70, and more preferably about 20 to about 45, peptidyl residues which have 100% contiguous amino acid sequence homology or identity to the amino acid sequence of a particular avian beta-defensin. For example, a preferred peptide of the invention is an avian beta-defensin peptide corresponding to SEQ ID NO:2, SEQ ID NO:4, SEQ ID NO:6, SEQ ID NO:8, SEQ ID NO:10, SEQ ID NO:12, SEQ ID NO:14, SEQ ID NO:16, a fragment or a derivative thereof. Moreover, it is envisioned that peptides within the scope of the invention may comprise moieties other than amino acid sequences which are derived from an avian beta-defensin, e.g., amino acid residues not present in the native avian beta-defensin (e.g., a fusion polypeptide), nucleic acid molecules or targeting moieties such as antibodies or fragments thereof, so long as these moieties do not substantially reduce the biological activity of the peptide. A substantial reduction in activity means a reduction in activity of greater than about 10%.

Preferably, the peptides of the invention are biologically active. For example, a "biologically active" peptide or variant thereof of the invention has at least about 1%, preferably at least about 10%, more preferably at least about 50%, and even more preferably at least about 90%, the activity of a peptide having, for example, SEQ ID NO:2, SEQ ID NO:4, SEQ ID NO:6, SEQ ID NO:8, SEQ ID NO:10, SEQ ID NO:12, SEQ ID NO:14 or SEQ ID NO:16. The activity of a peptide of the invention can be measured by methods well known to the art including, but not limited to, in vitro methods such as those described in Evans et al., *Vet. Micro.*, 47, 295 (1995); Harwig et al., *FEBS Lett.*, 342, 281 (1994); Evans et al., *J. Leuko. Biol.*, 56, 661 (1994); and U.S. Pat. No. 5,635,594, as well as the ability of the peptide to inhibit or reduce microbial growth when administered to an animal such as a bird, e.g., turkey or chicken, or a mammal, e.g., human, rabbit, dog, cat, goat, bovine, sheep, rat or mouse.

An isolated "variant" of a peptide of the invention is a peptide comprising no more than about 75, preferably about 10 to about 70, and more preferably about 20 to about 45, peptidyl residues which have at least about 50%, preferably at least about 80%, and more preferably at least about 90%, but less than 100%, contiguous amino acid sequence homology or identity to the amino acid sequence of the corresponding native avian beta-defensin. In addition to amino acids substitutions, a variant peptide of the invention may include, for example, amino-, carboxy- or internal deletions or additions relative to the corresponding native avian beta-defensin. Peptide variants include peptides having at least one D-amino acid. SModifications can also include, for example, substitutions with compounds that mimic amino acid structure or function.

Peptides or variants thereof which are subjected to chemical modifications, such as esterification, amidation, reduction, protection and the like, are referred to as "derivatives." For example, a modification known to improve the stability and/or bioavailability of peptides in vivo is the cyclization of the peptide, for example through one or more disulfide bonds. These peptides may then be converted to the cyclic peptides if desired by standard methods of cystine bond formation. "Cyclic forms" includes those forms which contain cyclic portions by virtue of the formation of disulfide linkages between cysteine residues in the peptide. One such modification is the synthesis of a cyclic reverse sequence derivative (CRD) of a peptide of the invention. A linear peptide is synthesized with all D-form amino acids using the reverse (i.e., C-terminal to N-terminal) sequence of the peptide. If necessary, additional cysteine residues are added to the N and C termini (if the peptide sequence does not already have N and C terminal cys residues), thereby allowing oxidative cyclization. However, the term "CRD" includes cyclization by other mechanisms, e.g., via a peptidyl bond, and the like.

Also included within the scope of the term "derivative" is linear reverse D (LRD) and cyclized forward L (CFL) derivatives. LRD derivatives have the reverse (i.e., C-terminal to N-terminal) sequence of the peptide with all D-form amino acids, but are not cyclized. CFL derivatives have the forward (i.e., N-terminal to C-terminal) sequence of the peptide with all L-form amino acids, but with additional N and C terminal cys residues (if the peptide sequence does not already have cys residues at either the N or the C terminal position), followed by oxidative cyclization, or cyclization by an alternative method.

An isolated "variant" nucleic acid molecule of the invention is a nucleic acid molecule which has at least 80%, preferably at least about 90%, and more preferably at least about 95%, but less than 100%, contiguous nucleotide sequence homology or identity to the nucleotide sequence of the corresponding wild type nucleic acid molecule, e.g., a DNA sequence comprising SEQ ID NO:1, SEQ ID NO:3, SEQ ID NO:5 or SEQ ID NO:7. Moreover, a variant nucleic acid molecule of the invention may include nucleotide bases not present in the corresponding wild type nucleic acid molecule, such as 5', 3' or internal deletions or additions relative to the corresponding wild type nucleic acid molecule. One example of such a modification is the addition of a restriction endonuclease site. Moreover, the term "variant" encompasses changes in non-coding regions.

As used herein, the terms "isolated and/or purified" refer to in vitro preparation, isolation and/or purification of a nucleic acid molecule, polypeptide or peptide of the invention, so that it is not associated with in vivo substances and is substantially free of infectious agents.

As used herein, the term "antimicrobial activity" refers to the ability of a compound to inhibit or irreversibly prevent the growth of a microorganism. Such inhibition or prevention can be through a microbicidal action or microbistatic inhibition. Therefore, the term "microbicidal inhibition" as used herein refers to the ability of the antimicrobial compound to kill, or irrevocably damage the target organism. The term "microbistatic inhibition" as used herein refers to the growth of the target organisms without death. Microbicidal or microbistatic inhibition can be applied to either an environment either presently exhibiting microbial growth (i.e., therapeutic treatment) or an environment at risk of supporting such growth (i.e., prevention or prophylaxis).

I. Nucleic Acid Molecules of the Invention

A. Sources of the Nucleic Acid Molecules of the Invention

Sources of nucleotide sequences from which the present nucleic acid molecules encoding avian beta-defensin, a fragment or a variant thereof, or the nucleic acid complement thereof, include RNA, or genomic DNA or cDNA from any avian, e.g., from physiological fluid or tissue such as bone marrow or purified heterophils, including chicken and turkey. Other sources of the DNA molecules of the invention include genomic or cDNA libraries derived from an avian. Moreover, the present DNA molecules also may be prepared in vitro, e.g., by synthesizing an oligonucleotide of about 215, preferably about 100, more preferably about 50, nucleotides in length, or by subcloning a portion of a DNA segment that encodes a particular avian beta-defensin.

B. Isolation of a Gene Encoding an Avian Beta-defensin

A nucleic acid molecule encoding an avian beta-defensin of the invention can be identified and isolated using standard methods, as described by Sambrook et al., *Molecular Cloning: A Laboratory Manual*, Cold Spring Harbor, N.Y. (1989). For example, reverse-transcriptase PCR (RT-PCR) can be employed to isolate and clone avian beta-defensin cDNAs. A primer which is complementary to an RNA encoding avian beta-defensin, and preferably hybridizes to the 3' two-thirds of the RNA, can be employed as a primer in a reverse transcriptase reaction to prepare first-strand cDNAs from isolated RNA which contains RNA sequences of interest, e.g., total RNA isolated from an infected avian tissue. RNA can be isolated by methods known to the art, e.g., using TRIZOL™ reagent (GIBCO-BRL/Life Technologies, Gaithersburg, Md.). Resultant first-strand cDNAs are then amplified in PCR reactions.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers comprising at least 7–8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp. Quant. Biol.*, 51, 263 (1987); Erlich, ed., *PCR Technology*, (Stockton Press, New York, 1989). Thus, PCR-based cloning approaches rely upon conserved sequences deduced from alignments of related gene or polypeptide sequences. However, other amplification-based methods known to the art may also be employed, including, but not limited to, self-sustained sequence-specific replication (3SR) (Gebinoga et al., *Eur. J. Biochem.*, 235, 256 (1996); Fahy et al., *PCR Methods Appl*, 1, 25 (1991); Guatelli et al., *Proc. Nat'l Acad. Sci. U.S.A.*, 87, 1874 (1990)), nucleic acid sequence-based amplification (NASBA) (Compton, *Nature*, 350, 91 (1991)), strand displacement amplification (SDA) (Walker et al., *Proc. Nat'l Acad. Sci. U.S.A.*, 89, 392 (1992); Walker et al., *Nucl. Acid Res.*, 20, 1691 (1992)), probe cyclization (Landgren, *Trends in Gen.*, 9, 199 (1993)), or a Q beta replicase, Sp6, T7, or T3 RNA polymerase based amplification system. See, for example, U.S. Pat. Nos. 5,622,820, 5,629,153, 5,532,126, 5,573,914 and 5,514,545.

Primers are made to correspond to highly conserved regions of peptides or nucleotide sequences which were identified and compared to generate the primers, e.g., by a sequence comparison of other beta-defensin genes or avian beta-defensin genes. One primer is prepared which is predicted to anneal to the antisense strand, and another primer prepared which is predicted to anneal to the sense strand, of a DNA molecule which encodes avian beta-defensin.

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs. Alternatively, the gel-purified fragment can be directly sequenced.

cDNA or genomic libraries can be screened using the colony hybridization procedure. Generally, each microtiter plate is replicated onto duplicate nitrocellulose filter papers and colonies are allowed to grow at 37° C. for 14–16 hours on L agar containing 50 μg/ml Amp. The colonies are lysed and DNA fixed to the filter by sequential treatment for 5 minutes with 500 mM NaOH, 1.5 M NaCl, and are washed twice for 5 minutes each time with 5×standard saline citrate (SSC). Filters are air dried and baked at 80° C. for 2 hours. The duplicate filters are prehybridized at 42° C. for 6–8 hours with 10 ml per filter of DNA hybridization buffer (5×SSC, pH 7.0, 5×Denhardt's solution (polyvinylpyrrolidine, plus Ficoll and bovine serum albumin; 1×=0.02% of each), 50 mM sodium phosphate buffer at pH 7.0, 0.2% SDS, 20 μg/ml Poly U, and 50 μg/ml denatured salmon sperm DNA).

The samples can be hybridized with kinased probe under conditions which depend on the stringency desired. Typical moderately stringent conditions employ a temperature of 42° C. for 24–36 hours with 1–5 ml/filter of DNA hybridization buffer containing probe. For higher stringencies, high temperatures and shorter times are employed. Generally, the filters are washed four times for 30 minutes each time at 37° C. with 2×SSC, 0.2% SDS and 50 mM sodium phosphate buffer at pH 7, then are washed twice with 2×SSC and 0.2% SDS, air dried, and are autoradiographed at −70° C. for 2 to 3 days.

As used herein, the terms "isolated and/or purified" refer to in vitro isolation of a nucleic acid molecule or peptide molecule from its natural cellular environment, and from association with other components of the cell, such as nucleic acid or polypeptide, so that it can be sequenced, replicated, and/or expressed. For example, "isolated avian beta-defensin nucleic acid" is RNA or DNA containing greater than 9, preferably 36, and more preferably 45 or more, sequential nucleotide bases that encode at least a portion of avian beta-defensin, or a variant thereof, or a RNA or DNA complementary thereto, that is complementary or hybridizes, respectively, to RNA or DNA encoding the avian beta-defensin and remains stably bound under stringent conditions, as defined by methods well known in the art, e.g., in Sambrook et al., supra. Thus, the RNA or DNA is "isolated" in that it is free from at least one contaminating nucleic acid with which it is normally associated in the natural source of the RNA or DNA and is preferably substantially free of any other RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source. An example of isolated avian beta-defensin nucleic acid is RNA or DNA that encodes an avian beta-defensin which shares at least about 70%, preferably at least about 80%, and more preferably at least about 90%, sequence identity with the avian beta-defensin polypeptide having SEQ ID NO:2, SEQ ID NO:4, SEQ ID NO:6, SEQ ID NO:8, SEQ ID NO:10, SEQ ID NO:12, SEQ ID NO:14, or SEQ ID NO:16.

As used herein, the term "recombinant nucleic acid" or "preselected nucleic acid," e.g., "recombinant DNA sequence or segment" or "preselected DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., *Nucleic Acids Res.*, 9, 6103 (1981), and Goeddel et al., *Nucleic Acids Res.*, 8, 4057 (1980). Therefore, "preselected DNA" includes completely synthetic DNA sequences, semi-synthetic DNA sequences, DNA sequences isolated from biological sources, and DNA sequences derived from RNA, as well as mixtures thereof.

As used herein, the term "derived" with respect to a RNA molecule means that the RNA molecule has complementary sequence identity to a particular DNA molecule.

C. Variants of the Nucleic Acid Molecules of the Invention

Nucleic acid molecules encoding amino acid sequence variants of avian beta-defensin or a variant thereof are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of avian beta-defensin.

Oligonucleotide-mediated mutagenesis is a preferred method for preparing amino acid substitution variants of avian beta-defensin. This technique is well known in the art as described by Adelman et al., *DNA*, 2, 183 (1983). Briefly, avian beta-defensin DNA is altered by hybridizing an oligonucleotide encoding the desired mutation to a DNA template, where the template is the single-stranded form of a plasmid or bacteriophage containing the unaltered or native DNA sequence of avian beta-defensin. After hybridization, a DNA polymerase is used to synthesize an entire second complementary strand of the template that will thus incorporate the oligonucleotide primer, and will code for the selected alteration in the avian beta-defensin DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. U.S.A.*, 75, 5765 (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.*, 153, 3 (1987). Thus, the DNA that is to be mutated may be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, New York, 1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of avian beta-defensin, and the other strand (the original template) encodes the native, unaltered sequence of avian beta-defensin. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for peptide or polypeptide production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-($\alpha$S) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-($\alpha$S) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101.

For example, a preferred embodiment of the invention is an isolated and purified DNA molecule comprising a preselected DNA segment encoding avian beta-defensin having SEQ ID NO:2, wherein the DNA segment comprises SEQ ID NO:1, or variants of SEQ ID NO:1, having nucleotide substitutions which are "silent" (see FIG. 4). That is, when silent nucleotide substitutions are present in a codon, the same amino acid is encoded by the codon with the nucleotide substitution as is encoded by the codon without the substitution. For example, valine is encoded by the codons GTT, GTC, GTA and GTG. A variant of SEQ ID NO:1 at the fourth codon in the prepro form of the polypeptide (GT<u>T</u> in SEQ ID NO:1) includes the substitution of GT<u>C</u>, GT<u>A</u> or GTA for GT<u>T</u>. Other "silent" nucleotide substitutions in SEQ ID NO:1 which can encode a polypeptide corresponding to SEQ ID NO:2 can be ascertained by reference to FIG. 4 and page D1 in Appendix D in Sambrook et al., *Molecular Cloning: A Laboratory Manual* (1989). Nucleotide substitutions can be introduced into DNA segments by methods well known to the art. See, for example, Sambrook et al., supra. Likewise, nucleic acid molecules encoding other avian beta-defensins may be modified in a similar manner. Thus, nucleic acid molecules encoding at least a portion of avian beta-defensin, or the complement thereto, may be modified so as to yield nucleic acid molecules of the invention having silent nucleotide substitutions, or to yield nucleic acid molecules having nucleotide substitutions that result in amino acid substitutions (see peptide variants hereinbelow).

II. Preparation of Expression Cassettes and Peptides Falling Within the Scope of the Invention

A. Nucleic Acid Molecules

1. Chimeric Expression Cassettes

To prepare expression cassettes for transformation herein, the recombinant or preselected DNA sequence or segment may be circular or linear, double-stranded or single-stranded. A preselected DNA sequence which encodes an RNA sequence that is substantially complementary to an RNA sequence encoding avian beta-defensin is typically a "sense" DNA sequence cloned into a cassette in the opposite orientation (i.e., 3' to 5' rather than 5' to 3'). Generally, the preselected DNA sequence or segment is in the form of chimeric DNA, such as plasmid DNA, that can also contain coding regions flanked by control sequences which promote the expression of the preselected DNA present in the resultant cell line.

As used herein, "chimeric" means that a vector comprises DNA from at least wo different species, or comprises DNA from the same species, which is linked or associated in a manner which does not occur in the "native" or wild type of the species.

Aside from preselected DNA sequences that serve as transcription units for avian beta-defensin, or portions thereof, a portion of the preselected DNA may be untranscribed, serving a regulatory or a structural function. For example, the preselected DNA may itself comprise a promoter that is active in the host cell, or may utilize a promoter already present in the genome that is the transformation target. Many promoter elements well known to the art may be employed in the practice of the invention.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers. A preferred promoter for expression in insect cells, e.g., Sf21 cells, is the polyhedron promoter.

Other elements functional in eukaryotic host cells, such as introns, enhancers, polyadenylation sequences and the like, may also be a part of the preselected DNA. Such elements may or may not be necessary for the finction of the DNA, but may provide improved expression of the DNA by affecting transcription, stability of the mRNA, or the like. Such elements may be included in the DNA as desired to obtain the optimal performance of the transforming DNA in the cell.

Yeast vectors often include the 2 micron origin of replication (Broach, J. R., *Meth. Enz.*, 101, 307 (1983)), although other plasmid vectors suitable for yeast expression are known (see, for example, Stinchcomb et al., *Nature*, 282, 39 (1979), Tschempe et al., *Gene*, 10, 157 (1980) and Clark, L. et al., 101, 300 (1983)). Control sequences for yeast vectors include promoters for the synthesis of glycolytic enzymes (Hess et al., *J. Adv. Enzyme Req.*, 7, 149 (1968); Holland et al., *Biochemistry*, 17, 4900 (1978)). Additional promoters known in the art include the promoter for 3-phosphoglycerate kinase (Hitzeman et al., *J. Biol. Chem.*, 255, 2073 (1980)), and those for other glycolytic enzymes such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization (Holland, ibid). It is also believed terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland, M. J. et al., *J. Biol. Chem.*, 256, 1385 (1981)) or the LEU2 gene obtained from YEp13 (Broach, J. et al., *Gene*, 8, 121 (1978)), however, any vector containing a yeast compatible promoter, origin of replication and other control sequences is suitable.

"Operably linked" is defined to mean that the nucleic acids are placed in a functional relationship with another nucleic acid sequence. For example, DNA for a presequence or secretory leader is operably linked to DNA for a peptide or polypeptide if it is expressed as a preprotein that participates in the secretion of the peptide or polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The preselected DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapa and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

Another sequence useful to prepare expression cassettes includes a signal sequence. This sequence is typically located immediately 5' to the nucleic acid encoding the peptide, and will thus be transcribed at the amino terminus of the fusion protein. However, in certain cases, the signal sequence has been demonstrated to be located at positions other than 5' to the gene encoding the protein to be secreted. This sequence targets the protein to which it is attached across the inner membrane of the bacterial cell. The DNA encoding the signal sequence can be obtained as a restriction endonuclease fragment from any nucleic acid encoding a peptide that has a signal sequence. Suitable prokaryotic signal sequences can be obtained from genes encoding, for example, Lamb or OmpF (Wong et al., *Gene*, 68, 193 (1983)), MalE, PhoA, OmpA and other genes. A preferred prokaryotic signal sequence for practicing this invention is the *E. coli* heat-stable enterotoxin II (STII) signal sequence as described by Chang et al., *Gene*, 55, 189 (1987).

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction.

2. Transformation into Host Cells

The recombinant DNA can be readily introduced into the host cells, either prokaryotic, e.g., bacterial, or eukaryotic, e.g., mammalian, plant, yeast or insect cells, by transfection with an expression vector comprising DNA encoding avian beta-defensin or its complement, by any procedure useful for the introduction into a particular cell, e.g., physical or biological methods (e.g., recombinant phage or viruses), to yield a transformed cell having the recombinant DNA stably integrated into its genome, so that the DNA molecules, sequences, or segments, of the present invention are expressed by the host cell. Prokaryotic hosts most frequently are represented by various strains of *E. coli*. However, other microbial strains may also be used, such as bacilli, for example, *Bacillus subtilis*, various species of Pseudomonas, or other bacterial strains. In such prokaryotic systems, plasmid vectors which contain replication sites and control sequences derived from a species compatible with the host are used.

Physical methods to introduce a preselected DNA into a host cell include calcium phosphate precipitation, lipofection, particle bombardment, microinjection, electroporation, and the like. The main advantage of physical methods is that they are not associated with pathological or oncogenic processes of viruses in eukaryotic hosts. However, they are less precise, often resulting in multiple copy insertions, random integration, disruption of foreign and endogenous gene sequences, and unpredictable expression.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of bacterial origin, but cell lines or host cells of mammalian origin may be employed, as well as plant, insect, yeast, or fungal sources. Generally, the preselected DNA sequence is related to a DNA sequence which is resident in the genome of the host cell but is not expressed, or not highly expressed, or, alternatively, overexpressed. Alternatively, the preselected DNA sequence is not related to a DNA sequence which is resident in the genome of the host cell. "Transfected" or "transformed" is used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence, which comprises a gene encoding avian beta-defensin or its complement, which host cell may or may not express significant levels of autologous or "native" avian beta-defensin.

To confirm the presence of the preselected DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular avian beta-defensin, e.g., by immunological means (ELISAs and Western blots) or by assays described herein.

To detect and quantitate RNA produced from introduced preselected DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the products of the introduced preselected DNA sequences or evaluating the phenotypic changes brought about by the expression of the introduced preselected DNA segment in the host cell.

B. Peptides, Variants, and Derivatives Thereof

The present isolated, purified peptides, variants or derivatives thereof, can be synthesized in vitro, e.g., by the solid phase peptide synthetic method or by recombinant DNA approaches (see above). When an avian beta-defensin DNA of the invention is expressed in a recombinant cell, it is necessary to purify the recombinant peptide from other cell proteins or polypeptides to obtain preparations that are substantially homogenous as to the recombinant avian beta-defensin. For example, the culture medium or lysate can be centrifuged to remove particulate cell debris. The membrane and soluble protein fractions are then separated. Avian beta-defensin may then be purified from the soluble protein fraction. Alternatively, avian beta-defensin may be purified from the insoluble fraction, i.e., refractile bodies (see, for example, U.S. Pat. No. 4,518,526), if necessary. Avian beta-defensin peptide may be purified from contaminant soluble or membrane proteins and polypeptides by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography, and the like.

If expressed as a fusion polypeptide, the fusion polypeptide may be purified by methods specific for the non-avian beta-defensin portion of the fusion polypeptide. For example, if the fusion polypeptide is a histidine tagged fusion polypeptide, Ni-NTA resin may be employed to purify the fusion polypeptide.

Avian beta-defensin, or a variant thereof, can also be prepared by in vitro transcription and translation reactions. An avian beta-defensin expression cassette can be employed to generate avian beta-defensin gene-specific transcripts which are subsequently translated in vitro so as to result in a preparation of substantially homogenous avian beta-defensin, variant avian beta-defensin, or a biologically active fragment thereof. The construction of vectors for use in vitro transcription/translation reactions, as well as the methodologies for such reactions, are well known to the art.

To prepare peptides or variants thereof of the invention, the solid phase peptide synthetic method is preferably employed. The solid phase peptide synthetic method is an established and widely used method, which is described in the following references: Stewart et al., *Solid Phase Peptide Synthesis*, W. H. Freeman Co., San Francisco (1969); Merrifield, *J. Am. Chem. Soc.*, 85 2149 (1963); Meienhofer in "Hormonal Proteins and Peptides," ed.; C. H. Li, Vol. 2 (Academic Press, 1973), pp. 48–267; and Bavaay and Merrifield, "The Peptides," eds. E. Gross and F. Meienhofer, Vol. 2 (Academic Press, 1980) pp. 3–285. These peptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Once isolated and characterized, derivatives, e.g., chemically derived derivatives, of a given recombinant avian beta-defensin peptide can be readily prepared. For example, amides of the avian beta-defensin, or a variant thereof may also be prepared by techniques well known in the art for converting a carboxylic acid group or precursor, to an amide. A preferred method for amide formation at the C-terminal carboxyl group is to cleave the peptide from a solid support with an appropriate amine, or to cleave in the presence of an alcohol, yielding an ester, followed by aminolysis with the desired amine.

Salts of carboxyl groups of a peptide or variant of the invention may be prepared in the usual manner by contacting the peptide or variant thereof with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of avian beta-defensin or a variant thereof may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the polypeptide, peptide or variant thereof. Other amino-terminal modifications include aminooxypentane modifications (see Simmons et al., *Science*, 276, 276 (1997)).

In addition, the amino acid sequence of a peptide of the invention can be modified so as to result in a variant. The modification includes the substitution of at least one amino acid residue in the polypeptide or peptide for another amino acid residue, including substitutions which utilize the D rather than L form, as well as other well known amino acid analogs. These analogs include ornithine, homoarginine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, citruline, α-methyl-alanine, para-benzoyl-phenylalanine, phenylglycine, propargylglycine, sarcosine, and tert-butylglycine.

One or more of the residues of the peptide can be altered, so long as the peptide variant is biologically active. For example, it is preferred that the variant has at least about 10% of the biological activity of the corresponding non-variant peptide, such as a peptide having SEQ ID NO:2.

Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids.

Conservative substitutions are shown in FIG. 5 under the heading of exemplary substitutions. More preferred substitutions are under the heading of preferred substitutions. After the substitutions are introduced, the variants are screened for biological activity.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into roups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic; trp, tyr, phe.

The invention also envisions peptide variants with non-conservative substitutions. Non-conservative substitutions entail exchanging a member of one of the classes described above for another.

Acid addition salts of amino residues of the peptide or variant thereof may be prepared by contacting the peptide or variant with one or more equivalents of the desired inorganic or organic acid, such as, for example, hydrochloric acid. Esters of carboxyl groups of the peptides or variants may also be prepared by any of the usual methods known in the art.

Other modifications include the reduction of cysteinyl thiol groups with 2-mercaptoethanol and carboxymethylated with iodoacetamide as described by Lambden et al. (1981).

Moreover, it is also envisioned that the peptides of the invention are modified in a manner that increases their stability in vivo. These modified agents are termed "derivatives." Methods to prepare such derivatives are well known to the art. One method is to prepare derivatives which are cyclized peptides (see EPA 471,453 (amide bonds); EPA 467,701 (disulfide bonds); EPA 467,699 (thioether bonds)). Other modifications are disclosed in Jameson et al. (*Nature*, 368, 744 (1994)); U.S. Pat. No. 4,992,463; and U.S. Pat. No. 5,091,396. For example, to cyclize peptides by oxidation of free cysteinyl thiol groups, peptide (0.1 mg ml$^{-1}$) is reacted for 1 hour at 0° C. with iodine (1 mM in methanol) and the oxidation is then quenched with sodium thiosulphate. The mixture is subjected to reverse-phase HPLC on a semi-preparative Zorbax C8 column, followed by gel filtration on a Zorbax GF250 column. Two peaks which are separated by the gel filtration step were further analyzed by mass spectroscopy, using an Applied Biosystems BioIon 20 Biopolymer plasma desorption time-of-flight Mass Analyzer. The first peak is resolved by mass analysis into two species, a partially protected monomer peptide and a dimeric peptide. The material is tested for free cysteine thiol groups with Ellman's reagent [5,5-dithio-bis(2-nitrobenzoic acid); Sigma] at the highest concentration of peptide before saturation (20 mg ml$^{-1}$). This peak represents the cyclic peptide and is stored at pH 4.0 at −20° C. until used (see Tam & Lu (1989)). A preferred embodiment of the invention is avian beta-defensin peptide or variant that has been cyclized by addition of one or more cysteine residues to the N and/or C terminus of the peptide with subsequent oxidation of the free cysteinyl thiol groups.

In all of the peptides of the invention, one or more amide linkages (—CO—NH—) may optionally be replaced with another linkage which is an isostere such as —CH$_2$NH—, —CH$_2$S—, —CH$_2$CH$_2$, —CH=CH— (cis and trans), —COCH$_2$—, —CH(OH)CH$_2$— and —CH$_2$SO—. This replacement can be made by methods known in the art. The following references describe preparation of peptide analogs which include these alternative linking moieties: A. F. Spatola, *Vega Data*, 1(3), "Peptide Backbone Modifications" (March 1983); A. F. Spatola, in "Chemistry and Biochemistry of Amino Acids Peptides and Proteins," B. Weinstein, eds., Marcel Dekker, New York, p. 267 (1983); J. S. Morley, *Trends Pharm. Sci.* (1980) pp. 463–468; D. Hudson et al., *Int J. Pept. Prot. Res.*, 14, 177–185 (1979) (—CH$_2$NH—), —CH$_2$CH$_2$—); A. F. Spatola et al., *Life Sci.*, 38, 1243–1249 (1986); (—CH$_2$—S); M. M. Hann, *J. Chem. Soc. Perkins Trans I*, 307–314 (1982) (—CH—CH—, cis and trans); R. G. Almquist et al., *J. Med. Chem.*, 23, 1392–1398 (1980); (—COCH$_2$—); C. Jennings-White et al., *Tetrahedron Lett.*, 23, 2533 (1982) (—COCH$_2$—); M. Szelke et al., European Application EP 45665 (1982) CA:97:39405 (1982) (—CH(OH) CH$_2$—); M. W. Holladay et al., *Tetrahedron Lett.*, 24, 4401–4404 (1983); (—C(OH) CH$_2$—); and V. J. Hruby, *Life Sci.*, 31, 189–199 (1982) (—CH$_2$—S—).

By "purified and isolated" is meant more than 90% pure, preferably more than 95% pure and more preferably more than 99% pure or is in a completely different context such as that of a pharmaceutical preparation.

III Dosages, Formulations and Routes of Administration of the Nucleic Acid Molecules and Peptides of the Invention Preparations comprising a peptide, or peptides, of the invention are preferably administered to a vertebrate, e.g., a bird such as a turkey or chicken or a human, in an amount effective to treat, inhibit, reduce, or prevent a microbial infection. These compounds and compositions can be administered to avians and mammals for veterinary use, such as for use with domestic or farm animals. For peptides of the invention, the dosage required is about 1 μg to about 10 mg, preferably about 10 μg to about 1 mg, and more preferably about 100 μg to about 500 μg, although other dosages may provide beneficial results. Dosages within these ranges can be administered via bolus doses or via a plurality of unit dosage forms, until the desired effects have been obtained. The amount administered will vary depending on various factors including, but not limited to, the specific peptide chosen, the weight, physical condition and age of the vertebrate, and the route of inoculation. Thus, for peptides, the absolute weight of the peptide included in a given unit dosage form can vary widely, and depends upon factors such as the species, age, weight and physical condition of the vertebrate, as well as the method of administration. Such factors can be readily determined by the veterinarian employing animal models or other test systems which are well known to the art.

Administration of the therapeutic agents in accordance with the present invention may be continuous or intermittent, depending, for example, upon the recipient's physiological condition, whether the purpose of the administration is therapeutic or prophylactic, and other factors known to skilled practitioners. Both local and systemic administration is contemplated. Systemic administration is preferred.

Administration of a sense or antisense nucleic acid molecule of the invention may be accomplished through the introduction of cells transformed with an expression cassette comprising the nucleic acid molecule (see, for example, WO 93/02556) or the administration of the nucleic acid molecule (see, for example, Felgner et al., U.S. Pat. No. 5,580,859, Pardoll et al., *Immunity*, 3, 165 (1995); Stevenson et al., *Immunol. Rev.*, 145, 211, (1995); Molling, *J. Mol. Med.*, 75, 242 (1997); Donnelly et al., *Ann. N.Y. Acad. Sci.*, 772, 40 (1995); Yang et al., *Mol. Med. Today*, 2, 476 (1996); Abdallah et al., *Biol. Cell*, 85, 1 (1995)). Pharmaceutical formulations, dosages and routes of administration for nucleic acids are generally disclosed, for example, in Felgner et al., supra.

Typically, compositions are prepared for injection or infusion, either as liquid solutions or suspensions. Solid forms suitable for solution in, or suspension in, liquid vehicles prior to injection or infusion may also be prepared. The preparation may also be emulsified. The active ingredient can be mixed with diluents, carriers or excipients which are physiologically acceptable and compatible with the active ingredient(s). Suitable diluents and excipients are, for example, water, saline, PBS, glycerol, or the like, and combinations thereof. In addition, if desired, the compositions may contain minor amounts of auxiliary substances such as wetting or emulsifying agents, stabilizing or pH-buffering agents, and the like.

Such compositions are conventionally administered parenterally, by injection. For example in birds, the composition may be administered intravenously, intramuscularly to breast, lung or thigh, subcutaneously via wing web injection, administration via the beak, spraying the animals or their environment, e.g., their housing or yard, or administration in the drinking water or feed. Formulations which are suitable for other modes of administration include suppositories, cloaca, insufflated powders or solutions, eye drops, nose drops, intranasal aerosols, and oral formulations.

For other vertebrates, one or more suitable unit dosage forms comprising the therapeutic agents of the invention, which, as discussed below, may optionally be formulated for sustained release (using, for example, liposomes, gels or hydrogels) can be administered by a variety of routes including oral, or parenteral, including by rectal, transdermal, subcutaneous, intravenous, intramuscular, intraperitoneal, intrathoracic, intrapulmonary and intranasal routes. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for oral administration, they are preferably combined with a pharmaceutically acceptable carrier, diluent or excipient to form a pharmaceutical formulation, or unit dosage form. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Pharmaceutical formulations containing the therapeutic agents of the invention can be prepared by procedures known in the art using well known and readily available ingredients. For example, the agent can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the agents of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing an agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric coated caplets or tablets of an agent of the invention are designed to resist disintegration in the stomach and dissolve in the more neutral to alkaline environment of the duodenum.

The therapeutic agents of the invention can also be formulated as elixirs or solutions for convenient oral administration or as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$–$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and α-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the agents are well suited to formulation as sustained release dosage forms and the like. The formulations can be so constituted that they release the active ingredient only or preferably in a particular part of the intestinal or respiratory tract, possibly over a period of time. The coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, and the like.

The therapeutic agents of the invention can be delivered via patches for transdermal administration. See U.S. Pat. No. 5,560,922 for examples of patches suitable for transdermal delivery of a therapeutic agent. Patches for transdermal delivery can comprise a backing layer and a polymer matrix which has dispersed or dissolved therein a therapeutic agent, along with one or more skin permeation enhancers. The backing layer can be made of any suitable material which is impermeable to the therapeutic agent. The backing layer serves as a protective cover for the matrix layer and provides also a support function. The backing can be formed so that it is essentially the same size layer as the polymer matrix or it can be of larger dimension so that it can extend beyond the side of the polymer matrix or overlay the side or sides of the polymer matrix and then can extend outwardly in a manner that the surface of the extension of the backing layer can be the base for an adhesive means. Alternatively, the polymer matrix can contain, or be formulated of, an adhesive polymer, such as polyacrylate or acrylate/vinyl acetate copolymer. For long-term applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 200 microns.

Generally, those polymers used to form the biologically acceptable adhesive polymer layer are those capable of forming shaped bodies, thin walls or coatings through which therapeutic agents can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix by skin moisture would affect the release rate of the therapeutic agents as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydro-gel), polyvinylidene chloride, poly(ethylene terephthalate), butyl rubber, epichlorohydrin rubbers, ethylenvinyl alcohol copolymers, ethylene-vinyloxyethanol copolymers; silicone copolymers, for example, polysiloxane-polycarbonate copolymers, polysiloxanepolyethylene oxide copolymers, polysiloxane-polymethacrylate copolymers, polysiloxane-alkylene copolymers (e.g., polysiloxane-ethylenesilane copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoroethylene; and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the therapeutic agent into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

Preferably, a plasticizer and/or humectant is dispersed within the adhesive polymer matrix. Water-soluble polyols are generally suitable for this purpose. Incorporation of a humectant in the formulation allows the dosage unit to absorb moisture on the surface of skin which in turn helps to reduce skin irritation and to prevent the adhesive polymer layer of the delivery system from failing.

Therapeutic agents released from a transdermal delivery system must be capable of penetrating each layer of skin. In order to increase the rate of permeation of a therapeutic agent, a transdermal drug delivery system must be able in particular to increase the permeability of the outermost layer of skin, the stratum corneum, which provides the most resistance to the penetration of molecules. The fabrication of patches for transdermal delivery of therapeutic agents is well known to the art.

For administration to the upper (nasal) or lower respiratory tract by inhalation, the therapeutic agents of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the therapeutic agent may be administered via nose drops, a liquid spray, such as via a plastic bottle atomizer or metered-dose inhaler. Typical of atomizers are the Mistometer (Wintrop) and the Medihaler (Riker).

For topical administration, the therapeutic agents may be formulated as is known in the art for direct application to a target area. Conventional forms for this purpose include wound dressings, coated bandages or other polymer coverings, ointments, creams, lotions, pastes, jellies, sprays, and aerosols. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1–25% by weight. Topical administration is one preferred route of administration of an agent of the invention.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The formulations and compositions described herein may also contain other ingredients such as other antimicrobial agents, or preservatives. Furthermore, the active ingredients may also be used in combination with other therapeutic agents, for example, bronchodilators.

The invention will be further described by reference to the following Example.

EXAMPLE I

Characterization of Beta-defensin Prepropeptide mRNA from Chicken and Turkey Bone Marrow Materials and Methods Animals and tissue sampling Six 3-week-old commercial broiler chickens and four broad-breasted white domestic turkey poults were humanely euthanized. Femurs and tibias were rapidly removed and split. Marrow samples were collected and placed in small cryostatic vials and immersed in liquid nitrogen.

Total RNA and mRNA Isolation and Analysis

Total cellular RNA was isolated from bone marrow by crushing marrow in liquid nitrogen to a fine powder with a mortar and pestle and extracting total RNA by the guanidium-thiocyanate method, Rapid Total RNA Isolation kit (5 Prime→3Prime, Inc., Boulder, Colo.) (Okayama et al., 1987; Sambrook et al., 1989). Total RNA samples were analyzed by spectrophotometry (DU-65 Series spectrophotometer, Beckman Instruments, Inc., Fullerton, Calif.) and electrophoresed through 1.2% RNase-free agarose electrophoretic gels (Chomczynski and Sacchi, 1987). Messenger RNA was isolated from total RNA samples using the Mini-Oligo(dt) Cellulose Spin Column Kit for Rapid Poly (A)+MRNA Preparation (5 Prime→3Prime, Inc.) (Ausubel et al., 1995; Sambrook et al, 1989). Spectrophotometric analysis was performed in order to assess the quantity and quality of mRNA samples.

Reverse Transcription, PCR and Sequence Analysis

A 100 ng sample of marrow mRNA was used to synthesize single stranded cDNA templates by reverse transcription (Stratagene RT-PCR, Stratagene, La Jolla, Calif.) using a polyA primer containing a specific tail sequence (Ela) (Table 1).

Degenerate intrapeptidal oligonucleotide primers (G2a+G2b and G1a+G1b) (Table 1) designed from the reported amino acid sequence of the mature antimicrobial peptides (Harwig et al., 1994; Evans et al., 1994) were used to amplify an 86 (Gal 2) and an 87 (Gal 1/CHP 1) base pair cDNA product, respectively (Table 1). Polymerase chain reaction was accomplished using an Idaho Technology Rapidcycler and Optimizer kit (Idaho Technology Inc., Idaho Falls, Id.). A 0.5 µl cDNA sample was placed in a 500 µl RNase-free microcentrifuge tube. Then, 10 µl of 40 mM MgCl$_2$, 10 µl of cresol red/sucrose (loading buffer), 1 µl of 10 mM dNTP's (Clontech), 1 µl of each primer (70 pmoles/µl), and sterile H$_2$O was added to attain a volume of 99.5 µl. Taq DNA polymerase (0.5 µl, 5 U/µl) (Promega, Madison, Wis.) was then added and the solution gently mixed. The mixture was sealed in 10 µl capillary tubes, placed on ice, and then placed into the Rapidcycler preheated to 94° C. for 15 seconds as a denaturing period. Cycling parameters were 35 cycles at 94° C. denaturing at 0 seconds, 40° C. annealing at 0 seconds, and 72° C. extension for 15 seconds, utilizing a slope of 0.2 (0.2° C. rise/s).

Cycled samples were placed directly into a 1.5% standard (Promega) ethidium bromide containing agarose electrophoretic gel mixed with 1×Tris/acetate/EDTA (TAE) buffer. Running voltage was 75 volts using 1×TAE as running buffer. Amplified PCR products were visualized by UV transilluminator (Ultra ◊ Lum) and fragments were purified using QIAEX II gel extraction kit or QIA quick gel extraction kit (Qiagen Inc., Chatsworth, Calif.) (Vogelstein and Gillespie, 1979).

Sequencing was performed by the Molecular Genetics Instrumentation Facility (MGIF), University of Georgia, using the Taq Dye Terminator cycle sequencing kit (Applied Biosystems division of Perkin-Elmer, Foster City, Calif.), following the manufacturer's protocol using an ABI-373 automated sequencer (Applied Biosystems). Sequences were analyzed using Gene Runner 3.03

(Hastings Software Inc.) for amino acid translation and for homology using National Center for Biotechnology Information (NCBI) BLAST network services [(http://www.ncbi.nlm.gov/cgi-bin/BLAST/nph-blast?Jform=0)].

After determination of a peptide sequence, a specific sense primer was designed from within this sequence. These primers were paired with the EPB antisense adapter primer (E1b) to amplify the region from the encoded peptide to the poly A tail. Amplification was accomplished as above, with the annealing temperature increased to 58° C. and the slope increased from 0.2 (0.2° C. rise/s) to 0.5 (0.5° C. rise/s).

A 5 prime RACE (Rapid Amplification of cDNA Ends) reaction, using the Marathon cDNA Amplification Kit (Clontech Laboratories, Inc., Palo Alto, Calif.), was used to amplify the 5 prime prepro region of Gal 2 and Gal 1/CHP 1 (Chenchik et al., 1995). Briefly, this was accomplished by preparing single stranded cDNA, then double stranded cDNA, and finally ligating modified adapters to each end of the double stranded cDNA. The configuration and specificity of these modified adapters, paired with a specific intrapeptidal primer, allowed amplification of the 5 prime region. Amplification was accomplished on the IT rapidcycler with the same conditions previously described. Samples were run, extracted, and sequenced.

Turkey poult marrow MRNA was prepared in the same manner described above. Primers G1c and G2c (Table 1) used to amplify turkey prepro peptides, THP 1 and THP 2, were designed from the chicken prepro regions. Both chicken primers were paired with the EPB antisense adapter primer (E1b) (Table 1) to produce nucleic acid sequences that included most of the prepro region, the entire mature peptide region, and the 3 prime nontranslated region extending to the poly A tail. The rest of the 5 prime region was amplified using the RACE reaction, then extracted, and sequenced.

Results

Four cDNA sequences encoding prepro beta-defensins Gallinacin 2 (Gal 2), Gallinacin 1 (Gal 1/CHP 1), and Turkey Heterophil Peptide 1 and 2 (THP 1 and THP 2) were characterized using degenerate intrapeptidal primers, specific intrapeptidal primers, adapter primers, prepro region primers, and 5-prime RACE amplification. The amplified cDNAs encoding prepro peptides Gal 2, THP 2, Gal 1/CHP 1, and THP 1 ranged from 409 to 494 nucleic acid residues (FIG. 1). Deduced amino acid sequences for the mature peptides were consistent with reported complete or partial peptide sequences (Harwig et al., 1994; Evans et al., 1994). Although one set of degenerate primers (G1a+G1b; Table 1) could have amplified either Gal 1/CHP 1 and/or Gal 1α/CHP 2 because of their extensive similarity, only CDNA for Gal 1/CHP 1 was amplified. Previously reported Gal 1/CHP 1 mature peptide sequences ended with either tryptophan (W) or arginine (R) (Harwig et al., 1994; Evans et al., 1994). The deduced Gal 1/CHP 1 mature peptide sequence ended with a glycine (G), following tryptophan (W) and preceding the stop codon (FIG. 1).

TABLE 1

Oligonucleotide primers

| Oligonucleotide Primers | | Sequences |
|---|---|---|
| EPBdt18 polyA primer (SEQ ID NO: 17) | (E1a) | GCG-AAT-TCT-GCA-GGA-TCC-AAA-CT$_{16}$ |
| EPB antisense adapter primer (SEQ ID NO: 18) | (E1b) | GCG-AAT-TCT-GCA-GGA-TCC-AAA-C |
| Gal 2 sense degenerate primer (SEQ ID NO: 19) | (G2a) | TGY-CAY-TTY-GGI-GGI-TGY-CC |
| Gal 2 antisense degenerate primer (SEQ ID NO: 20) | (G2b) | GCR-TTC-CAI-GGC-CAY-TTR-CA |
| Gal 1 sense degenerate primer (SEQ ID NO: 21) | (G1a) | GGI-TTY-TGY-GCI-TTY-YTI-AAR-TGY-CC |
| Gal 1 antisense degenerate primer (SEQ ID NO: 22) | (G1b) | CCA-DAT-ICK-YTT-RCA-RCA |
| Gal 2 sense prepro primer for THP 2 (SEQ ID NO: 23) | (G2c) | GCA-CTC-CAG-GTT-TCT-CCA-GGG-TTG |
| Gal 1 sense prepro primer for THP 1 (SEQ ID NO: 24) | (G1c) | ATG-CGG-ATC-GTG-TAC-CTG-CTC |

Y = C, T; R = A, G; D = G, A, T; K = G, T; I = Inosine

The prepro region primer designed from chicken Gal 2 cDNA amplified THP 2 cDNA from turkey marrow, whereas the prepro region primer designed from Gal 1/CHP 1 cDNA amplified a product corresponding with THP 1 from turkey marrow (FIG. 1). The prepropeptide mRNA sequences of each pair of chicken and turkey beta-defensins are remarkably similar (FIG. 1). Complete prepro peptides, Gal 1/CHP 1 and THP 1, contained 65 amino acids, differing at 16 amino acids and 30 nucleic acid residues (85% homology). Whereas, Gal 2 and THP 2 each contained 64 amino acids, differing at 5 amino acids and 13 nucleic acid residues (93.2% homology) (FIG. 1).

All peptide prepro regions began with a methionine, indicating the beginning of the signal sequence. The first AUG in each sequence is flanked by a canonical Kozak box. The initiating sequences of the prepro peptides, AUG (CAGCCAUG) SEQ ID NO:53 for Gal 2 and THP 2 and AUG(AAACCAUG) SEQ ID NO:54 for Gal 1/CHP 1 and THP1 (FIG. 2), agree reasonably well with consensus sequence (CCACCAUG) previously described (Kozak, 1987).

The nucleic acid sequences of Gal 2 and THP 2 showed homology to those encoding the TAP pre region at 46 of 67 nucleic acids (n.a.) (68% homology), whereas Gal 1/CHP 1 showed homology in the pre region of TAP at 67 of the 118 n.a. (56% homology) (FIG. 1). Gal 2 and THP 2 pre regions also had homology to RatNP-4 (Rat Neutrophil Peptide-4) at 44 of 62 n.a.=70%, RatNP-1 and 2 (Rat Neutrophil Peptide-1 and 2) at 42 of 59 n.a.=71%, bovine lingual antimicrobial peptide at 44 of 67 n.a.=65%, and HNP-4 (Human Neutrophil Peptide-4) at 39 of 55 n.a.=70%.

Positive and negatively charged amino acid groups contained in the prepro region are: Gal 2 and THP 2 (+4/−1) and Gal 1/CHP 1 and THP 1 (+2/0) would not neutralize the positive charges in the mature peptides; Gal 2, THP 2, Gal 1/CHP 1 or THP 1 (+6/0; +8/−1; +9/−1; +8/−1); respectively (FIG. 2).

Discussion

Avian beta-defensins Gal 2, THP 2, Gal 1/CHP 1, and THP 1 cDNAs predict deduced translation products containing 64, 64, 65, and 65 amino acid residues, respectively (FIG. 1). Each precursor peptide is composed of a signal sequence, a basic or neutral propiece, and the mature peptide sequence (from about 36 to about 40 residues).

The beta-defensin cDNA sequence compositions were most similar to storage granule-free epithelial cell beta-defensins, TAP or LAP, rather than mammalian classical defensin storage granule archetype, consisting of signal piece (about 19 amino acid residues and hydrophobic), propiece (>40 amino acid residues and highly acidic), and mature peptide (cationic). However, this is the first report of prepro peptide sequences for beta-defensins that are stored in granulated leukocytes.

The biological role of the propiece is not fully understood, but inactivation of the mature peptide by the propiece has been demonstrated in vitro (Valore et al., 1996). Targeting of the propeptide into the appropriate subcellular organelles and assisting in the correct folding of the mature peptide also has been demonstrated (Liu et al., 1995). The storage granule contains the proregion and the classical defensin. This negatively charged proregion appears to neutralize the positive (basic) charge of the classical defensin mature peptide and consequently the cytotoxicity during post-translational processing (Michaelson et al., 1992). The avian beta-defensin mature peptide has a similar positive charge but no long, neutralizing, negative, proregion. Negative charges are not present in the proregion of THP 1 or Gal 1/CHP 1, whereas Gal 2 and THP 2, have one negative charge. Overall, there are 0 to 2 negative charges in each propeptide, which is similar to beta-defensins, TAP and LAP (FIG. 2). This charge distribution differs from strongly negative classical defensin propieces in storage granules. Even the deduced cDNA sequences that have been isolated from granulated Paneth cells possess a deduced full-length negatively charged proregion, similar to those found in myeloid classical defensins (Jones and Bevins, 1993). Therefore, avian leukocytes may possess some other mechanism for charge neutralization and the mechanism of granule targeting may be different than that for classical defensins. For example, some other negatively charged protein may neutralize the negative charge of the beta-defensins.

Only partial amino acid sequences have been previously recovered and reported for the turkey beta-defensins. Primers designed from the chicken sequences allowed full amplification and characterization of the turkey mRNA. This led to the analysis and subsequent complete deduced amino acid sequence of two, turkey beta-defensins. The avian heterophil may be useful to study post-translational processing and storage of beta-defensins in granulated cells.

EXAMPLE II

Production of Avian β-defensin Fusion Proteins in the Baculovirus Expression System The cDNA sequences for the avian β-defensins gallinacin 2 (Gal 2) and turkey heterophil peptide 2 (THP 2) have been cloned in pCR II plasmids. The gallinacin cDNA insert was cut from the pCRII vector, agarose gel purified, extracted, and ligated into the multiple cloning site of the pBlueBac His2B vector (FIG. 6). *E. coli* INV-alpha F' was transformed and recombinant clones were selected for ampicillin resistance. Plasmid preparations of recombinant clones were prepared and presence of inserts confirmed by PCR using gallinacin-specific and vector-specific primers. The correct sequences and reading-frames of inserts were confirmed by primer extension sequencing. The same methods were used to construct a recombinant BlueBac His2B transfer vector with a turkey heterophil peptide 2 cDNA insert.

Figure 7A:
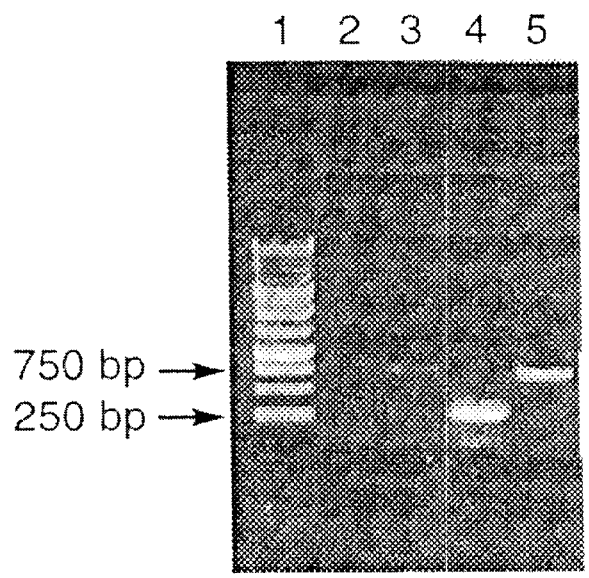
FIG. 7. Agarose gel electrophoresis of PCR products generated from baculovirus clones. (A) Lane 1, DNA molecular weight markers; Lane 2, wild-type virus without recombinant insert amplified by turkey heterophil peptide 2-specific primers; Lane 3, wild-type virus amplified with forward and reverse baculovirus PCR primers (predicted fragment size 839 bp); Lane 4; recombinant virus, clone THP2.2, amplified with turkey heterophil peptide 2-specific primer; Lane 5, recombinant virus amplified with forward and reverse baculovirus PCR primers (predicted fragment size 765 bp). (B) Lane 1, DNA molecular weight markers; Lane 2, wild-type virus without recombinant insert ampli- fied with gallinacin 2-specific primers; Lane 3, wild-type virus amplified with forward and reverse baculovirus PCR primers (predicted fragment size 839 bp); Lane 4; recombinant virus, clone Gal 2.3, amplified with gallinacin 2-specific primer; Lane 5, recombinant virus amplified with forward and reverse baculovirus PCR primers (predicted fragment size 642 bp).
Figure 7B:
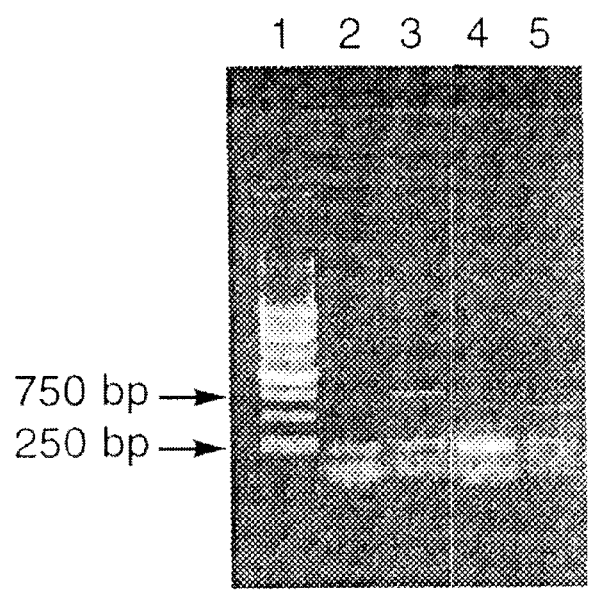

Each recombinant baculovirus transfer vector was recombined with linearized [Bac-N-Blue™] BAC-N-BLUE™ DNA (AcMNPV) to generate a recombinant virus. The recombinant baculoviruses were used to transfect Sf9 insect cells. Lac Z positive occlusion body-negative clones were selected. PCR was conducted using two sets of primers (turkey heterophil peptide 2- and gallinacin 2-specific primers) to confirm the presence of the proper inserts (FIG. 7). Also, forward and reverse baculovirus PCR primers were used to amplify segments of wild-type DNA or segments of recombinant virus containing the inserts. All PCR products approximated the size that was predicted.

Figure 9:
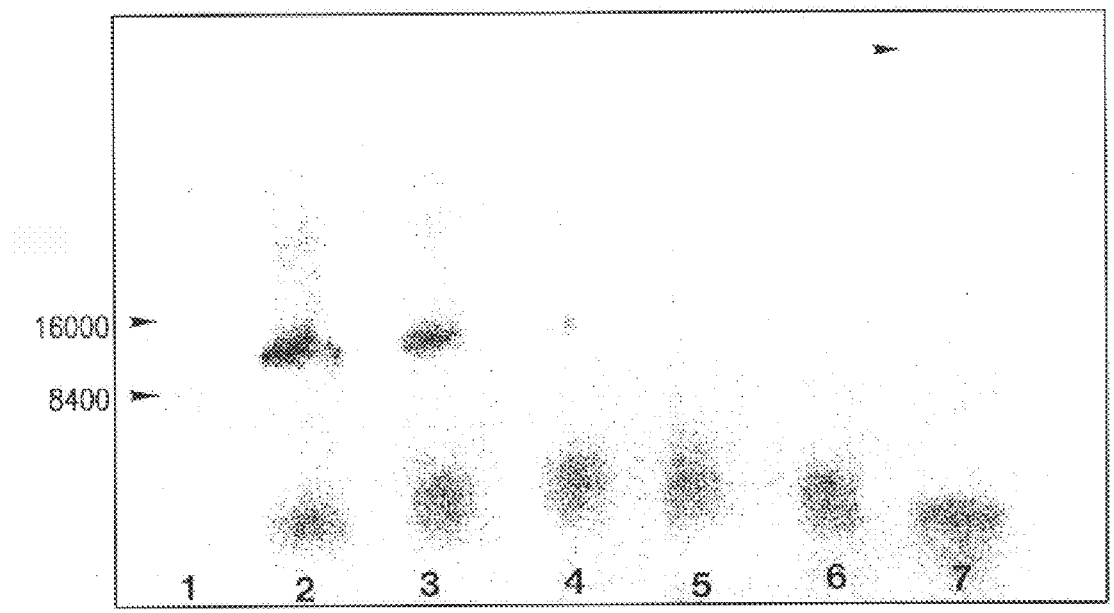
FIG. 9. Western blot from SDS tricine gel of cell lysates harvested from High-five™ insect cells infected with recombinant baculovirus encoding the His-tagged Gal-2 fusion protein. Samples were taken at 12 hr intervals following infection to demonstrate increased expression of the late promoted fusion protein over time. The blot was probed with anti-RGS-His antibody, specific for the His-tagged portion of the protein. Lane 1=molecular weight markers, Lane 2=84 hrs after infection, Lane 3=72 hrs, Lane 4=60 hrs, Lane 5=48 hrs, Lane 6=36 hrs after infection, and Lane 7=positive control His-tagged protein (arrowhead).

Viral stocks of each clone were produced and the sequence for the THP 2 insert confirmed in a P3 viral stock (FIG. 8). This data confirm that both avian β-defensin cDNAs are present in baculovirus stocks. A high-titer viral stock of both recombinant viruses was used to infect cells, and the fusion protein from cell lysates detected using anti-RGS-His antibodies on Western blots (FIG. 9).

REFERENCES

Ausubel, F. M., Brent, R., Kingston, R. E., Moore, D. D., Seidman, J. G., Smith, J. A., Struhl, K., eds., *Current Protocols in Molecular Biology*, John Wiley & Sons, Inc., New York, N.Y., 4.5.1.–4.5.3 (1995).

Belcourt, D., Singh, A., Bateman, A., Lazure, C., Solomon, S., and Bennett, H. P. J., "Purification of Cationic Cysteine-Rich Peptides from Rat Bone Marrow. Primary Structures and Biologic Activity of the Rat Corticostatin Family of Peptides," *Regulatory Peptides*, 40, 87–100 (1992).

Chenchik, A., Moqadam, F., Siebert, P., "Marathon cDNA Amplification: A New Method for Cloning Full Length cDNAs," *CLONTECHniques*, X (1), 5–8 (1995).

Chomczynski, P., Sacchi, N., "Single-step Method of RNA Isolation by Acid Guanidinium Thiocyanate-Phenol-Chloroform Extraction," *Analytical Biochemistry*, 162, 156 (1987).

Diamond, G., Zasloff, M., Eck, H., Brasseur, M., Maloy, W. L., Bevins, C. L., "Tracheal Antimicrobial Peptide, a Cysteine-Rich Peptide from Mammalian Tracheal Mucosa: Peptide Isolation and Cloning of a cDNA," *Proceedings of the National Academy of Sciences of the USA*, 88, 3952–3956 (1991).

Evans, E. W. "Isolation of cationic antimicrobial peptides from chicken heterophils" Ph.D. Thesis, University of Georgia, 1994.

Evans, E. W., Beach, F. G., Moore, K. M., Jackwood, M. W., Glisson, J. R., Harmon, B. G., "Antimicrobial Activity of Chicken and Turkey Heterophil Peptides CHP1, CHP2, THP1, and THP3," *Veterinary Microbiology*, 47, 295–303 (1995).

Evans, E. W., Beach, G. G., Wunderlich, J., Harmon, B. G., "Isolation of Antimicrobial peptides from Chicken Heterophils," *J. of Leukocyte Biology*, 56, 661–665 (1994).

Harwig, S. S. L., Swiderek, K. M., Kokryakov, V. N., Tan, L., Lee, T. D., Panyutich, E. A., Aleshina, G. M., Shamova, O. V., Lehrer, R. I., "Gallinacins: Cysteine-rich Antimicrobial Peptides of Chicken Leukocytes," *FEBS Letters*, 342, 281–285 (1994).

Jones, D. E., Bevins, C. L., "Defensin-6 mRNA in Human Paneth Cells: Implications for Antimicrobial Peptides in Host Defense of the Human Bowel," *FEBS Letters*, 31, 187–192 (1993).

Kokryakov, V. N. et al., *FEBS*, 31, 231–236 (1993).

Kozak, M., "An Analysis of 5'-noncoding Sequences from 699 Vertebrate Messenger RNAs," *Nucleic Acids Research*, 15, 8125–8132 (1987).

Lehrer, R. I. et al., *Cell*, 64, 229–230 (1991).

Lehrer, R. I. et al., *Ann. Rev. Immunol.*, 11, 105–128 (1993).

Liu, L., Ganz, T., "The Pro Region of Human Neutrophil Defensin Contains a Motif that is Essential for Normal Subcellular Sorting," *Blood*, 85, 1095–1103 (1995).

Martin, E., Ganz, T., Lehrer, R. I., "Defensins and Other Endogenous Peptide Antibiotics of Vertebrates," *J. of Leukocyte Biology*, 58, 128–136 (1995).

Michaelson, D., Rayner, J., Couto, M., Ganz, T., "Cationic Defensins Arise from Charge-Neutralized Propeptides: a Mechanism for Avoiding Leukocyte Autocytotoxicity?", *J. of Leukocyte Biology*, 51, 634–639 (1992).

Montali, R. J., "Comparative Pathology of Inflammation in the Higher Vertebrates (Reptiles, Birds, and Mammals)," *J. of Comparative Pathology*, 99, 1–21 (1988).

Nakamura, T. et al., *J. Biol. Chem.*, 26, 16709–16713 (1988).

Okayama, H., Kawaichi, M., Brownstein, M., Lee, F., Yokota, T., Arai, K., *Methods Enzymology*, R. Wu and L. Grossman, eds., Academic Press, San Diego, Calif., 154, 3–28 (1987).

Pennial, R., Spitznagel, J. K., "Chicken Neutrophils: Oxidative Metabolism in Phagocytic Cells Devoid of Myeloperoxidase," *Proceedings of the National Academy of Sciences of the USA*, 72, 5012–5015 (1975).

Russell, J. P., Diamond, G., Tarver, A. P., Scanlin, T. F., Bevins, C. L., "Coordinate Induction of Two Antibiotic Genes in Tracheal Epithelial Cells Exposed to the Inflammatory Mediators Lipopolysaccharide and Tumor Necrosis Factor Alpha," *Infection and Immunity*, 64, 1565–1568 (1996).

Sambrook, J., Fritsch, E. F., Maniatis, T., "Molecular Cloning: A Laboratory Manual," 2nd edition, Cold Springs Harbor Laboratory Press, Cold Springs Harbor, N.Y., 7.19–7.22 (1989).

Sambrook, J., Fritsch, E. F., Maniatis, T., "Molecular Cloning: A Laboratory Manual," 2nd edition, Cold Springs Harbor Laboratory Press, Cold Springs Harbor, N.Y., 7.3–7.4, 7.26–7.28 (1989).

Schonwetter, B. S., Stolzenberg, E. D., Zasloff, M. A., Epithelial Antibiotics Induced at Sites of Inflammation," *Science*, 267, 1645–1648 (1995).

Selsted, M. E., Harwig, S. S. L., "Purification, Primary Structure, and Antimicrobial Activities of a Guinea Pig Neutrophil Defensin," *Infection and Immunity*, 55, 2281–2286 (1987).

Selsted, M. E., Tang, Y., Morris, W. L., McGuire, P. A., Novotny, M. J., Smith, W., Henschen, A. H., Cullor, J. S., "Purification, Primary Structures, and Antibacterial Activities of β-defensins, a New Family of Antimicrobial Peptides from Bovine Neutrophils," *J. of Biological Chemistry*, 268, 6641–6648 (1993).

Valore, E. V., Martin E., Harwig, S. S. L., Ganz, T., "Intramolecular Inhibition of Human Defensin HNP-1 by its Propiece," *J. of Clinical Investigations*, 97, 1624–1629 (1996).

Vogelstein, B., Gillespie, D., "Preparative and Analytical Purification from Agarose," *Proceedings of the National Academy of the USA*, 76, 615–619 (1979).

Wilde, G. C., Griffith, J. E., Marra, M. N., Snable, J. L., Scott, R. W., "Purification and Characterization of Human Neutrophil Peptide 4, a Novel Member of the Defensin Family," *J. of Biological Chemistry*, 264, 11200–11203 (1989).

Yount, N. Y., Wang, M. C., Yuan, J., Banaiee, N., Ouellette, A. J., Selsted, M. E., "Rat Neutrophil Defensins: Precursor Structures and Expression During Neutrophilic Myelopoiesis," *J. of Immunology*, 155, 4476–4484 (1995).

Zimmermann, G. R., Legault, P., Selsted, M. E., Pardi, A., "Solution Structure of Bovine Neutrophil β-Defensin-12: The Peptide Fold of the β-Defensins is Identical to that of the classical Defensins, *Biochemistry*, 34, 13663–13671 (1995).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated and purified nucleic acid molecule comprising a nucleic acid sequence which encodes an avian beta-defensin polypeptide having SEQ ID NO:8.

2. An isolated and purified nucleic acid molecule comprising SEQ ID NO:7.

3. An isolated and purified nucleic acid molecule encoding residues 29 to 64 of SEQ ID NO:8.

4. The nucleic acid molecule of claim 2 which consists of SEQ ID NO:7.

5. An isolated and purified nucleic acid molecule which is fully complementary to SEQ ID NO:7.

6. An expression c sette comprising the isolated and purified nucleic acid molecule of claim 1, 2, 3 or 4 which is operably linked to a promoter for expression of the nucleic acid molecule in a host cell.

7. The expression cassette of claim 6 further comprising a nucleic acid segment operably linked to the isolated and purified nucleic acid molecule so as to encode a fusion polypeptide.

8. The expression cassette of claim 7 wherein the isolated and purified nucleic acid molecule encodes residues 29 to 64 of SEQ ID NO:8 and the nucleic acid segment encodes a heterologous signal peptide.

9. The expression cassette of claim 6 wherein the host cell is a prokaryotic cell.

10. The expression cassette of claim 6 wherein the host cell is a eukaryotic cell.

11. A method of using a nucleic acid molecule, said method comprising expressing the nucleic acid molecule of claim 1 in a cultured host cell stably transformed with a chimeric vector comprising said nucleic acid molecule operably linked to control sequences recognized by the host cell so as to yield a polypeptide encoded by the nucleic acid molecule of claim 1.

12. A method of using a nucleic acid molecule, said method comprising expressing the nucleic acid molecule of claim 2 in a cultured host cell stably transformed with a chimeric vector comprising said nucleic acid molecule operably linked to control sequences recognized by the host cell so as to yield a polypeptide encoded by the nucleic acid molecule of claim 2.

13. The method of claim 11 or 12 further comprising recovering the polypeptide from the host cell.

14. An isolated host cell comprising the expression cassette of claim 6.

15. An expression cassette comprising the isolated and purified nucleic acid molecule of claim 5 which is operably linked to a promoter for expression of the nucleic acid molecule in a host cell.

* * * * *

UNITED STATES PATENT AND TRADEMARK OFFICE
CERTIFICATE OF CORRECTION

PATENT NO.        : 6,545,140 B1                                       Page 1 of 1
APPLICATION NO. : 09/351657
DATED             : April 8, 2003
INVENTOR(S)       : Harmon et al.

It is certified that error appears in the above-identified patent and that said Letters Patent is hereby corrected as shown below:

In column 55, line 43, in Claim 6, delete "Anexpression" and
insert -- An expression --, therefor.

In column 55, line 43, in Claim 6, delete "c settle" and insert -- cassette --, therefor.

Signed and Sealed this

Fourteenth Day of November, 2006

JON W. DUDAS
*Director of the United States Patent and Trademark Office*